US012665478B2

(12) United States Patent
Kant et al.

(10) Patent No.:  US 12,665,478 B2
(45) Date of Patent:      Jun. 23, 2026

(54) BEARINGLESS SPLIT TEETH FLUX REVERSAL MOTOR

(71) Applicant: Massachusetts Institute of Technology, Cambridge, MA (US)

(72) Inventors: Krishan Kant, Cambridge, MA (US); David L. Trumper, Plaistow, NH (US)

(73) Assignee: Massachusetts Institute of Technology, Cambridge, MA (US)

( * ) Notice: Subject to any disclaimer, the term of this patent is extended or adjusted under 35 U.S.C. 154(b) by 271 days.

(21) Appl. No.: 18/530,495

(22) Filed: Dec. 6, 2023

(65) Prior Publication Data

US 2024/0195276 A1     Jun. 13, 2024

Related U.S. Application Data

(60) Provisional application No. 63/430,856, filed on Dec. 7, 2022.

(51) Int. Cl.
| | |
|---|---|
| *H02K 21/40* | (2006.01) |
| *A61M 60/109* | (2021.01) |
| *A61M 60/216* | (2021.01) |
| *A61M 60/422* | (2021.01) |
| *F04D 7/00* | (2006.01) |
| *F04D 13/06* | (2006.01) |
| *H02K 1/17* | (2006.01) |
| *H02K 1/24* | (2006.01) |

(52) U.S. Cl.
CPC ........... *H02K 21/40* (2013.01); *A61M 60/109* (2021.01); *A61M 60/216* (2021.01); *A61M 60/422* (2021.01); *F04D 7/00* (2013.01); *F04D 13/06* (2013.01); *H02K 1/17* (2013.01); *H02K 1/246* (2013.01)

(58) Field of Classification Search
CPC .......... H02K 21/40; H02K 1/17; H02K 1/246; A61M 60/109; A61M 60/216; A61M 60/422; F04D 7/00; F04D 13/06
See application file for complete search history.

(56) References Cited

U.S. PATENT DOCUMENTS

| | | | |
|---|---|---|---|
| 6,355,998 B1 | 3/2002 | Schob et al. | |
| 10,833,570 B2 * | 11/2020 | Noh ..................... | H02K 11/215 |
| 12,264,945 B2 | 4/2025 | Welsch et al. | |

(Continued)

FOREIGN PATENT DOCUMENTS

| | | | | | |
|---|---|---|---|---|---|
| CN | 106787569 A | * | 5/2017 | ............. | H02K 1/141 |
| CN | 112290767 A | * | 1/2021 | ............. | H02K 21/14 |

OTHER PUBLICATIONS

CN-106787569-A_translate (Year: 2017).*

(Continued)

*Primary Examiner* — Tulsidas C Patel
*Assistant Examiner* — Mohammed Ahmed Qureshi
(74) *Attorney, Agent, or Firm* — Daly, Crowley, Mofford & Durkee, LLP

(57)     ABSTRACT

A bearingless split tooth flux-reversal motor (FRM) for use with a pump, such as a centrifugal blood pump. In some embodiments, the motor has a magnet-free rotor and a magnetic configuration wherein the force generation is independent of the rotor angle, allowing for simple radial force generation using stator-fixed currents. The motor torque can be generated using commutated two-phase currents.

20 Claims, 17 Drawing Sheets

(56) References Cited

U.S. PATENT DOCUMENTS

2023/0304831 A1    9/2023  Straubinger et al.
2024/0035856 A1    2/2024  Hamazaki

OTHER PUBLICATIONS

CN-112290767-A_translate (Year: 2021).*
Bourque et al., "Design Rationale and Preclinical Evaluation of the HeartMate 3 Left Ventricular Assist System for Hemocompatibility"; American Society for Artificial Internals Organs Journal, vol. 62(4); May 2016; pp. 375-383 (9 pages).
Schoeb et al., "Principle and Application of a Bearingless Slice Motor"; JSME International Journal, Series C, vol. 40, No. 4; Aug. 1996; p. 2. 593-598 (6 pages).
Schob et al., "The Bearingless Centrifugal Pump—A Perfect Example of a Mechatronics System"; IFAC Proceedings vols. vol. 33, Issue 26; 2000; pp. 443-448 (6 pages).
Chiba et al., "Characteristics of a Bearingless Induction Motor"; IEEE Transactions on Magnetics, vol. 27, No. 6; Nov. 1991; pp. 5199-5201 (3 pages).
Takemoto et al., "Improved Analysis of a Bearingless Switched Reluctance Motor"; IEEE Transactions on Industry Applications, vol. 37, No. 1; Jan./Feb. 2001; pp. 26-34 (9 pages).
Holenstein et al., "Performance Benchmarking of a Novel Magnet-Free Bearingless Synchronous Reluctance Slice Motor"; IEEE Open Journal of the Industrial Electronics Society, vol. 1,; Jul. 2020; pp. 184-193 (10 pages).
Gruber et al., "Bearingless Slice Motor Concepts Without Permanent Magnets in the Rotor"; 2013 IEEE International Conference on Industrial Technology (ICIT); 2013; pp. 259-265 (7 pages).
Turk et al., "Nonlinear Control of a Bearingless Flux Switching Slice Motor With Combined Winding System"; IEEE/ASME Transactions on Mechatronics, vol. 25, No. 1; Feb. 2020; pp. 152-163 (12 pages).
Holenstein et al., "A Wide Air Gap Flux Switching Bearingless Motor with Odd and Even Pole Pair Numbers"; IEEE Open Journal of Industry Applications, vol. 1; Jul. 2020; pp. 52-62 (11 pages).
Noh et al., "Hysteresis Bearingless Slice Motors With Homopolar Flux-Biasing"; IEEE/ASME Transactions on Mechatronics, vol. 22, No. 5; Oct. 2017; pp. 2308-2318 (11 pages).
Noh et al., "Homopolar Bearingless Slice Motor With Flux-Biasing Halbach Arrays"; IEEE Transactions on Industrial Electronics, vol. 67, No. 9; Sep. 2020; pp. 7757-7766 (10 pages).
Deodhar et al., "The Flux-Reversal Machine: A New Brushless Doubly-Salient Permanent-Magnet Machine"; IEEE Transactions on Industry Applications, vol. 33, No. 4; Jul./Aug. 1997; pp. 925-934 (10 pages).

Kant et al., "A Novel Bearingless Interior Permanent Magnet Slice Motor for Pump"; 9th IFAC Symposium on Mechatronic Systems (Mechatronics 2022); Nov. 2022 (10 pages).
Raggl et al., "A Comparison of Separated and Combined Winding Concepts for Bearingless Centrifugal Pumps"; JPE Journal of Power Electronics, vol. 9, No. 2; Feb. 2009; pp. 243-258 (16 pages).
Zhu et al., "Analysis of Back-EMF in Flux-Reversal Permanent Magnet Machines by Air Gap Field Modulation Theory"; IEEE Transactions on Industrial Electronics, vol. 66, No. 5; May 2019; pp. 3344-3355 (12 pages).
Gruber et al., "Bearingless Segment Motor with Buried Magnets"; Journal of System Design and Dynamics, 2009, vol. 3, Issue 5; Oct. 2009; pp. 704-716 (13 pages).
Nguyen et al., "Modeling and Control of Salient-Pole Permanent Magnet Axial-Gap Self-Bearing Motor"; IEEE/ASME Transactions on Mechatronics, vol. 16, No. 3; Jun. 2011; pp. 518-526 (9 pages).
Zwyssig et al., "High-Speed Magnetically Levitated Reaction Wheel Demonstrator"; Proceedings of the International Power Electronics Conference—ECCE Asia (IPEC 2014), May 2014; pp. 1707-1714 (8 pages).
Zhou et al., "Magnetically Levitated Linear Stage With Linear Bearingless Slice Hysteresis Motors"; IEEE/ASME Transactions on Mechatronics, vol. 26, No. 2; Apr. 2021; pp. 1084-1094 (11 pages).
Kurita et al., "A Study on a Double Stator Type Axial Magnetically Levitated Motor"; IEEE International Symposium on Industrial Electronics; May 2013; pp. 1-5 (5 pages).
Kant et al., "Rotor design for 2 Pole Bearingless Interior Permanent Magnet Slice motor"; 2021 IEEE Energy Conversion Congress and Exposition (ECCE); 2021; pp. 4632-4638 (7 pages).
Khamitov et al., "Comparison of Combined Winding Strategies for Radial Nonsalient Bearingless Machines"; IEEE Transactions on Industry Applications, vol. 57, No. 6; Nov.-Dec. 2021; pp. 6856-6869 (14 pages).
Silber et al., "Design Aspects of Bearingless Slice Motors"; IEEE/ASME Transactions on Mechatronics, vol. 10, No. 6; Dec. 2005; pp. 611-617 (7 pages).
Larsonneur et al., "New Radial Sensor For Active Magnetic Bearings"; Ninth International Symposium on Magnetic Bearings; Aug. 2004; (5 pages).
Noh et al., "Low-cost Eddy-current Position Sensing for Bearingless Motor Suspension Control"; 2017 IEEE International Electric Machines and Drives Conference (IEMDC), 2017; (6 pages).
Laithwaite et al., "Magnetic equivalent circuits for electrical machines"; Proceedings of the Institution of Electrical Engineers, 1967, vol. 114, No. 11; Nov. 1967; pp. 1805-1809 (5 pages).
Office Action dated Nov. 20, 2025, for U.S. Appl. No. 18/532,118; 14 pages.

* cited by examiner

500

504

508

506a
506b

502

B [tesla]

2.0000
1.8183
1.6885
1.5587
1.4289
1.2991
1.1692
1.0394
0.9096
0.7798
0.6500
0.5202
0.3904
0.2606
0.1308
0.0010

1200

1400

1402b

1404a

1402b

1404b

BEARINGLESS SPLIT TEETH FLUX REVERSAL MOTOR

CROSS-REFERENCE TO RELATED APPLICATIONS

This application claims the benefit under 35 U.S.C. § 119 of U.S. Provisional Patent Application No. 63/430,856 filed on Dec. 7, 2022, which is hereby incorporated by reference herein in its entirety.

STATEMENT REGARDING FEDERALLY SPONSORED RESEARCH

This invention was made with government support under HL134455 awarded by the National Institutes of Health. The government has certain rights in the invention.

BACKGROUND

Extracorporeal blood pumps are used for various procedures like blood oxygenation, dialysis, and platelet separation. The tubing, pump housing, impeller, and other components that come in contact with the blood are only used once to avoid clumping and infection. In bearingless motors, where the rotor integrated with impeller is levitated and spun for pumping, the rotor also becomes a disposable component.

Bearingless motors with permanent magnet (PM) rotors are dominantly used for blood pumps. The use of permanent magnets makes these rotors relatively expensive and difficult to recycle. It is also not convenient to separate the magnets from the rotor for reuse. Typically, after single use, a PM rotor is discarded.

SUMMARY

There are two broad classes of motors with magnet-free rotor: one in which the whole motor is magnet-free, and another in which only the rotor is magnet-free with magnets present in the stator. Induction motors and switched/synchronous reluctance motors fall into the first class. While these motors satisfy the magnet-free requirement, they have some limitations for blood pump application. For example, induction motors may experience rotor losses due to slip, which can be harmful in certain applications such as blood pump applications (as the heat will be dissipated in the blood and can damage blood cells). Switched/synchronous reluctance motors do not have the slip problem, but since all the magnetic flux is generated using currents, they may suffer from lesser torque constant. Other issues with these motors, even in slice configuration, is that the passive magnetic stiffness is generated by the windings and a small airgap is generally required to be an effective motor. A continuous current is required to maintain levitation against gravity as well, which increases ohmic loss in the motor.

The aforementioned issues can be solved by adding magnets in the stator while maintaining a magnet-free rotor. Magnets in the stator provide bias flux, which enhances the force and torque constant and provides passive magnetic stiffness. Some such motors operate using airgap flux harmonics, while others operate using a different principle like flux-biased hysteresis.

Efforts have been made to design homopolar and conventional bearingless flux-switching motors. These motors may have certain desirable features, such as high torque density, immunity to demagnetization, better thermal management, and sinusoidal back electromotive force. However, the radial electromagnetic force required for position control is non-linear with respect to the rotor angle. Thus, sophisticated position control may be required, where force-angle mapping is used to control the rotor position depending on the rotor angle.

Another motor topology that has been proposed for bearingless application is flux-reversal motor (FRM). FRM may be attractive for traction motor applications owing to features like robust rotor, sinusoidal back EMF, bipolar flux variation, and easier thermal design attributed to both winding and magnets present on stator, however the radial force for bearingless operation is nonlinear for this type of motor as well.

In contrast to prior motor designs, embodiments described herein utilize a motor topology featuring magnets attached to the face of stator teeth which provides better flexibility in modifying the stator than the flux-switching motor. This provides for an easy-to-control flux-reversal bearingless motor.

Described herein are various embodiments of a bearingless split-tooth flux-reversal slice motor topology that can be used, for example, in blood pump applications. Also described herein are motor systems in which the split-tooth topology may be employed, and techniques controlling the same (e.g., closed loop position control and speed control).

According to the present disclosure, a bearingless split-tooth flux-reversal slice motor can have a magnetic configuration wherein the force generation is independent of the rotor angle. Single phase/single coil force generation characteristics of the motor can be non-linear and can depend on rotor angular position. Hence, the motor may be designed to generate the radial force along two axes (X and Y) independent of the rotor angular orientation. This makes the suspension control simpler, and suspension can be attained like a homopolar motor with DC currents.

A bearingless split-tooth flux-reversal slice motor according to the present disclosure may achieve torque and force specifications required by extracorporeal blood pumps, along with other parameters like cogging torque and magnetic stiffness. The general motor design presented herein can be adjusted to achieving various force and torque requirements, for example, by varying the slot/pole combination. In some examples, combined motor windings may be used in which each stator tooth has a coil and is independently excited with combined suspension and torque current components. This helps in utilizing the windings efficiently.

According to one aspect of the disclosure, a motor includes a stator and a magnet-free rotor having one or more salient features. The stator includes a plurality of split teeth, each split tooth including a first coil winding and a second coil winding. One or more of the split teeth include: a first tooth portion that includes the first coil winding and a first permanent magnet having a first polarity and a second tooth portion that includes the second coil winding and a second permanent magnet having a second polarity opposite the first polarity. The motor is configured to drive current through the first coil winding and the second coil winding to levitate the magnet-free rotor using a magnet-biased reluctance actuator principle and to rotate the magnet-free rotor using a flux-reversal operating principal. The motor is further configured to generate torque and rotational force independently.

In some embodiments, the motor may be provided as a bearingless split-tooth slice motor. In some embodiments, the motor can be configured to drive a blood pump. In some embodiments, flux of a first one of the plurality of split teeth is configured to be controlled independently from flux of other ones of the plurality of split teeth. In some embodiments, the one or more of the split teeth and their corresponding first permanent magnet and second permanent magnet can be arranged such that at least some adjacent permanent magnets have opposite polarity. In some embodiments, for the one or more of the split teeth, one or both of the first permanent magnet and the second permanent magnet may be attached to an end of the corresponding tooth portion. In some embodiments, for the one or more of the split teeth, one or both of the first permanent magnet and the second permanent magnet can have a dimension that is wider than a dimension of the corresponding tooth portion. In some embodiments, for the one or more of the split teeth, one or both of the first permanent magnet and the second permanent magnet can have a dimension that is equal to a dimension of the corresponding tooth portion. In some embodiments, for the one or more of the split teeth, one or both of the first permanent magnet and the second permanent magnet may have a dimension that is longer than a dimension of the stator.

In some embodiments, the rotor can have a plurality of poles separated by about 35°. In some embodiments, one or more of the plurality of split teeth can have multiple coils. In some embodiments, one or more of the plurality of split teeth may be configured as temple stator teeth. In some embodiments, for one or more of the plurality of split teeth, the first and second permanent magnets can be buried in the respective first and second tooth portions.

In some embodiments, the motor can further a controller configured to drive current through the coil windings of the plurality of split teeth to levitate and rotate the magnet-free rotor and to independently generate torque and rotational force on the magnet-free rotor. In some cases, the rotor can be levitated using a magnet-biased reluctance actuator principle and/or rotated using a flux-reversal operating principal.

According to one aspect of the disclosure, a system includes a pump driven by a bearingless split-tooth slice motor.

It should be appreciated that individual elements of different embodiments described herein may be combined to form other embodiments not specifically set forth above. Various elements, which are described in the context of a single embodiment, may also be provided separately or in any suitable sub-combination. It should also be appreciated that other embodiments not specifically described herein are also within the scope of the following claims.

BRIEF DESCRIPTION OF THE DRAWINGS

The manner of making and using the disclosed subject matter may be appreciated by reference to the detailed description in connection with the drawings, in which like reference numerals identify like elements.

The drawings are not necessarily to scale, or inclusive of all elements of a system, emphasis instead generally being placed upon illustrating the concepts, structures, and techniques sought to be protected herein.

DETAILED DESCRIPTION

Figure 1A:
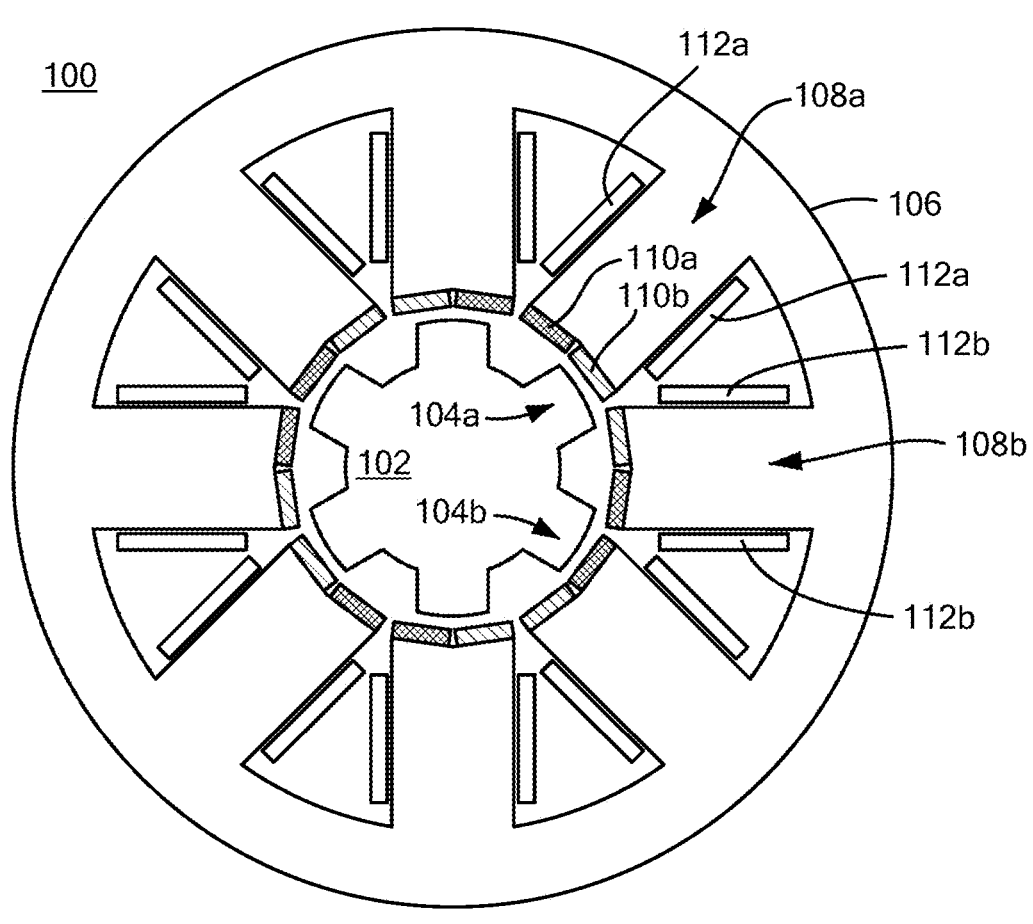
FIG. 1A is a top view of a conventional flux-reversal motor (FRM) topology.

FIG. 1A shows a conventional flux-reversal motor (FRM) topology 100. A conventional FRM motor can include a rotor 102 having a plurality of poles 104a, 104b, etc. (104 generally) and a stator 106 having a plurality of teeth 108a, 108b, etc. (108 generally). In the example of FIG. 1A, there are six (6) poles 104 and eight (8) teeth 108 (sometimes referred to as "slots"). Each stator tooth 108 has a pair of permanent magnets (PMs) of alternate polarity. For example, stator tooth 108a includes a first magnet 110a having a given polarity (e.g., north) and second magnet 110b having the opposite polarity (e.g., south). In the figure, all magnets shown in solid (e.g., magnet 110a) are assumed to have the same polarity and all magnets shown in hatching (e.g., magnet 110b) are assumed to have the same opposite polarity. This convention is used in subsequent figures as well. Coils 112a, 112b, etc., (112 generally) are wound around stator teeth 108a, 108b, etc., respectively. While coils 112 are shown only the sides of each stator tooth 108, it should be understood that each coil 112 wraps arounds all sides of its respective stator tooth 108.

The conventional flux-reversal motor can generate torque by interaction of flux density harmonics generated by the modulation of stator winding 112 and permanent magnets 110 flux by the rotor 102 in the airgap. The topology 100 of FIG. 1 may be described as having a 4-pole 2-phase stator winding and a 8-pole permanent magnet arrangement. The 4-pole pair permanent magnet flux density gets modulated by the six (6) rotor teeth 104, thereby effectively also creating 2-pole pair and 10-pole pair flux densities in the airgap. This modulated flux density interacts with the 2-pole pair stator winding flux and creates the torque. Additional harmonics in the airgap create torque in either direction, but the explanation for torque generation holds for all these harmonic components and net torque is calculated by combining all those where PM airgap flux and stator winding flux feature the same harmonic order. The theory of suspension force generation for the FRM is same as the PM motors.

Figure 1B:
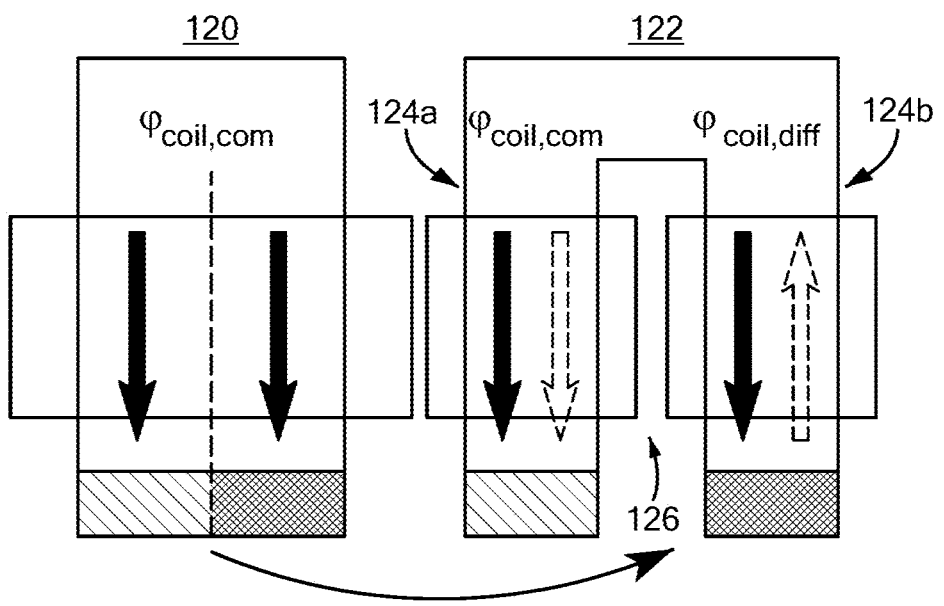
FIG. 1B illustrates how each stator tooth with alternate polarity magnets is split into teeth with independent coils and magnets, according to embodiments of the present disclosure.

Turning to FIG. 1B, according to embodiments of the present disclosure, the conventional FRM topology can be improved using a split-tooth design. The disclosed topology relies on the same torque generation principle is same as the conventional, but a different principle of force generation. The suspension force can be generated utilizing the flux-biased actuator structure of the flux-reversal topology. Since each stator tooth has magnets of both polarity and a coil, the coil excitation reduces the flux from one magnet and enhances it from the other. However, to generate force in one direction, the overall flux from one stator teeth should be either increased or decreased, which is not feasible with a conventional FRM topology.

To achieve this, according to the present disclosure, each stator tooth can split into two and wound separately so that the flux of each magnet can be controlled independently. This is illustrated in FIG. 1B, as a conventional FRM tooth 120 is split into two parts, resulting in a pair of teeth 122 having a first part 124a and a second part 124b separated by gap 126. Each part 124a, 124b of the split pair of teeth 122 has an independent coil (i.e., a coil not coupled to any other coil) and a magnet, as shown. This approach can be understood in terms of common winding flux ($\varphi_{coil,com}$) and differential winding flux ($\varphi_{coil,diff}$) which are illustrated by solid arrows and dashed arrows, respectively, in the figure. Common winding flux is required to generate torque and differential flux is required to generate force. Since each split tooth has a magnet of different polarity, the common flux adds to the magnetic flux of one magnet and reduces the flux from the other. While the differential flux either adds or reduces the magnetic flux of both magnets of opposite polarity. Hence, it either reduces or enhances the net flux for one pair of split stator teeth 122 as shown in FIG. 1B. This arrangement resembles a permanent magnet biased reluctance actuator.

Figure 1C:
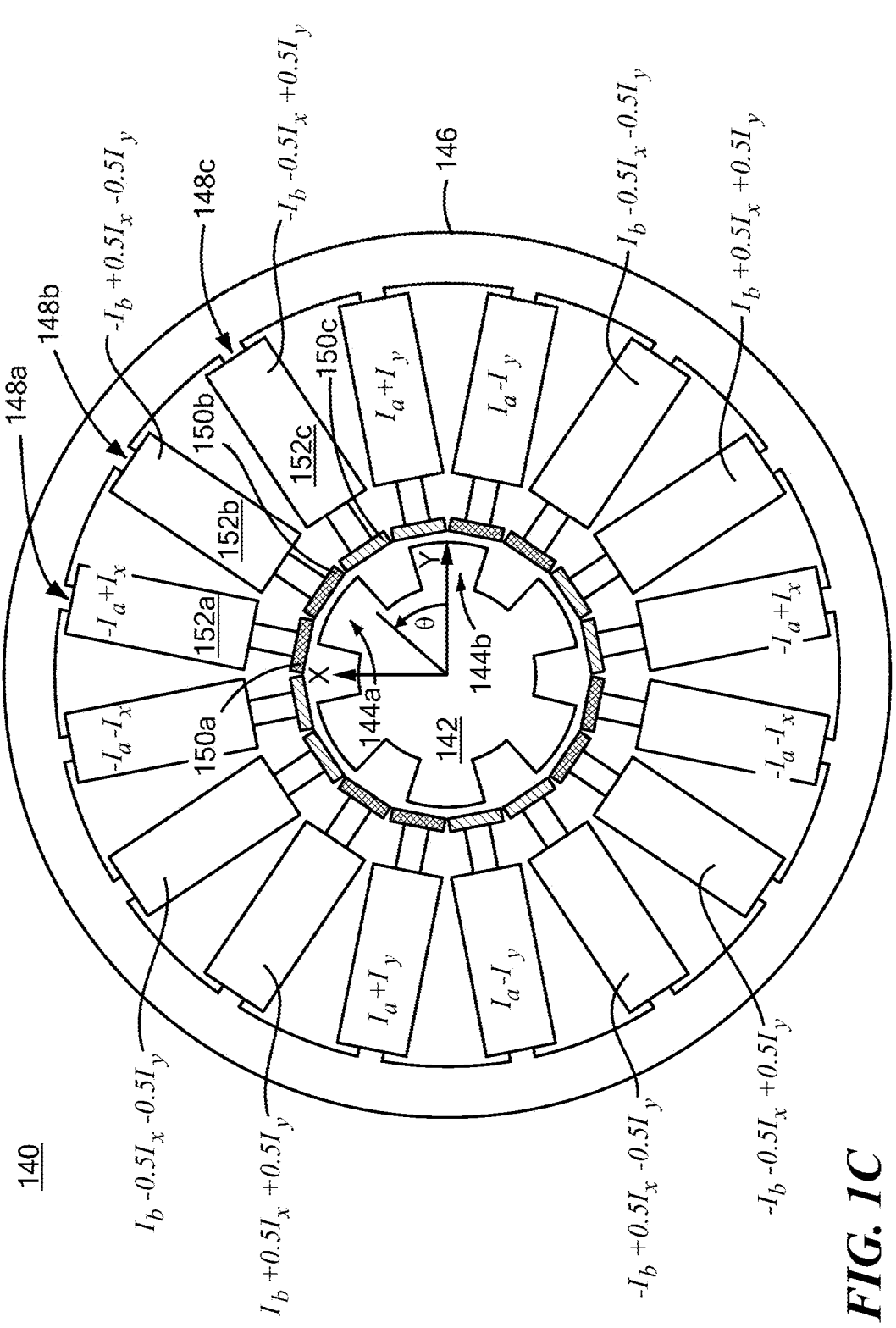
FIG. 1C is a top view of a split-tooth flux-reversal motor topology, according to some embodiments.

Turning to FIG. 1C, a split-tooth flux-reversal motor topology is shown where each stator tooth features an independent coil and a magnet. Illustrative topology 140 includes a rotor 142 having a plurality of poles 144a, 144b, etc. (144 generally) and a stator 146 having a plurality of teeth 148a, 148b, 148c, etc. (148 generally). In the example of FIG. 1C, there are six (6) poles 144 and sixteen (16) total teeth 148 which can be viewed as eight teeth each split into two parts. The poles 144 and teeth 148 can be symmetrical arranged around the rotor 142 and stator 146, respectively. Permanent magnets 150a, 150b, 150c, etc. (150 generally) are each attached at an end of a respective one of the stator teeth 148a, 148b, 148c, etc., as shown. Magnets 150 can include NdFEB N45 magnets, for example. Each of the stator teeth 148a, 148b, 148c, etc. has a respective one of coils 152a, 152b, 152c, etc. (152 generally) wound therearound. Thus, each stator tooth 148 features an independent coil 152 and a magnet 150.

In the figure, all magnets shown in solid (e.g., magnets 150a and 150b) are assumed to have the same polarity and all magnets shown in hatching (e.g., magnet 150c) are assumed to have the same opposite polarity. Half of the magnets 150 can have one polarity and the other half have opposite polarity. In the example of FIG. 1C, a pair of adjacent stator teeth may have magnets of the same polarity followed by a pair of adjacent stator teeth having magnets of the same, opposite polarity.

The combined windings along with excitation is also shown. $I_{xy}$ are suspension currents in X/Y direction and Iab are the 2-phase motor currents. Having magnets that are wider than the stator teeth, as in FIG. 1C, or magnets in between the stator teeth, as in FIG. 1D, helps with the cogging toque and somewhat with force and torque capability.

The topology 140 of FIG. 1C—having eight (8) stator slots (sixteen (16) after splitting) and six (6) rotor teeth—may represent the topology with minimum number of stator teeth which can satisfy force and torque requirements for certain applications, such as extracorporeal blood pumps. However, the general split-tooth flux-reversal slice motor topology disclosed herein may have other slot/pole combinations that can generate torque with 2- or 3-phase source and can generate force in 2-axes independent of the rotor angle, which simplifies the suspension control.

After splitting each stator tooth, there are sixteen (16) teeth with sixteen (16) coils. This winding arrangement can be a combined winding scheme where each coil carries motor current as well as suspension current. With four (4) pole pair magnets in the stator and six (6) rotor teeth, a two (2) pole pair stator winding may be required to produce torque. Before splitting the FRM stator teeth, eight (8) stator teeth can allow a symmetric 2-pole pair winding in a 2-phase configuration. After splitting the teeth, the current can be assigned to corresponding winding. This defines the current assignment for torque generation as shown in FIG. 1C.

A pair of adjacent stator teeth with opposite magnet polarity creates a set of PM biased actuator and generates the force in that direction. This direction defines the suspension axis as shown in FIG. 1C. Four of these teeth pairs create the force along the orthogonal axes while the rest of the teeth are used to generate forces in both axes, such that the net force in any axis is independent of the rotor angle. The idea is that magnetomotive force (MMF) generated by X or Y current experiences an approximately constant rotor pole area with rotation. Thus the force generation is not affected by rotation. One such winding configuration and force current assignment is shown in FIG. 1C. The X and Y DC currents can be distributed equally in the off axes (not along X/Y) winding such that the winding current does not exceed its rated value.

In FIG. 1C, X,Y correspond to levitation axes, The aligned and misaligned rotor orientations can be defined as a rotor pole completely aligned (as with X) or completely misaligned (as with Y). This definition may be used for control and design purposes.

In some cases, an electromagnetic position sensor may be used for levitation position control of a bearingless split-tooth flux-reversal slice motor. The rotor position can be measured with a sensor, located under rotor 142, which operates using electromagnetic sensing of 6-degrees of freedom. For example, position sensors described U.S. Provisional Patent Application 63/386,441 filed on Dec. 7, 2022, incorporated herein by reference, may be used in conjunction with the motor topology 140 of FIG. 1C.

Figure 1D:
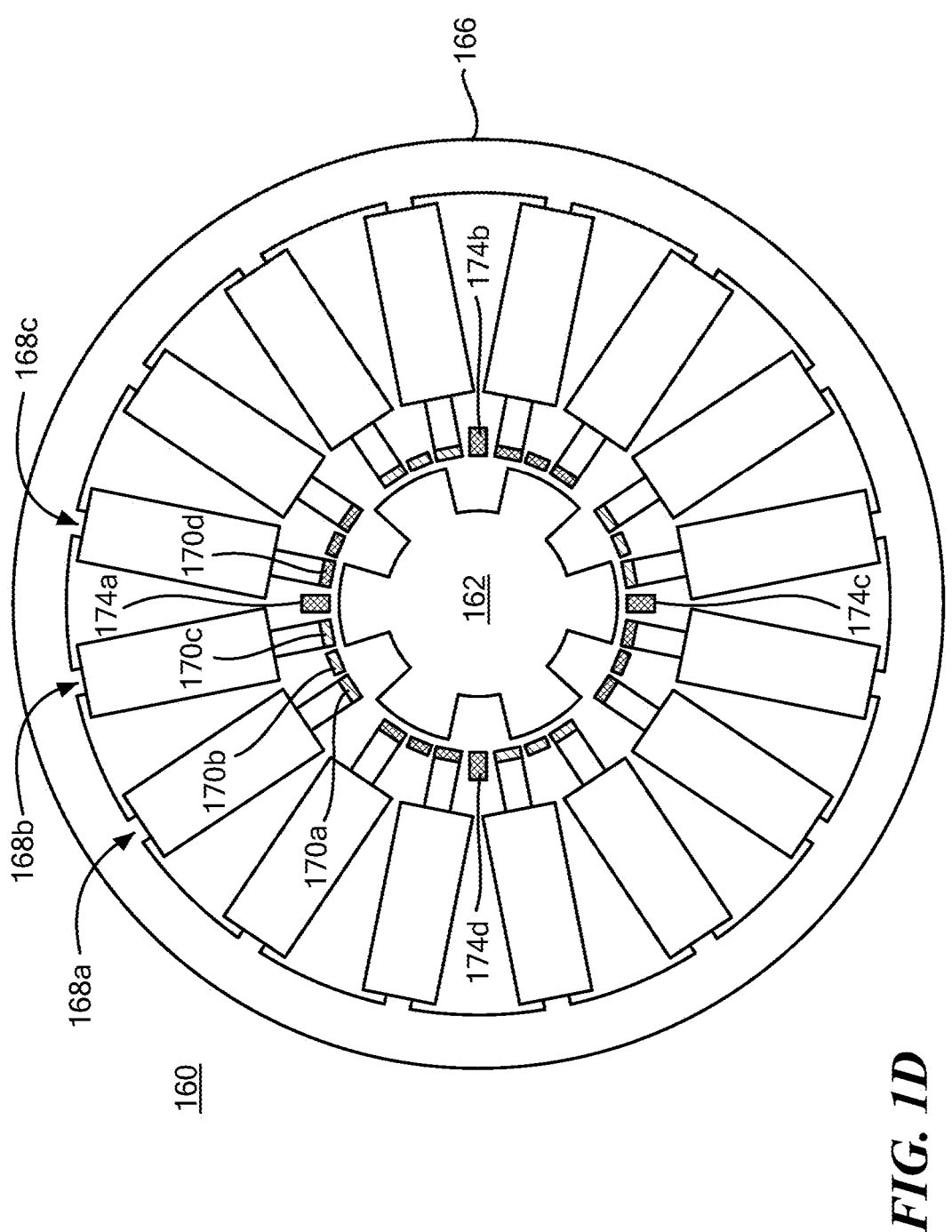
FIG. 1D is a top view of a split-tooth flux-reversal motor adapted to accommodate optical sensors, according to some embodiments.

Turning to FIG. 1D, in some cases, a bearingless split-tooth flux-reversal slice motor 160 can be provided with optical position sensors 174a, 174b, 174c, 174d (174 generally) arranged to measure position at the rotor surface periphery in the airgap between rotor 162 and stator 166. These sensors may be used, for example, in conjunction with an electromagnetic position sensor to provide redundancy. The arrangement of magnets 170a, 170b, 170c, 170d, etc. can be modified to accommodate optical sensors 174 in the stator slots (e.g., optical sensor 174a is positioned between stator teeth 168b and 168c). For example, as shown, two magnets 170a and 170c may be attached to the ends of adjacent stator teeth 160a and 160b, respectively, and a third magnet 170b may be attached between magnets 170a and 170c, where all three magnets 170a-c have the same polarity.

Figure 2:
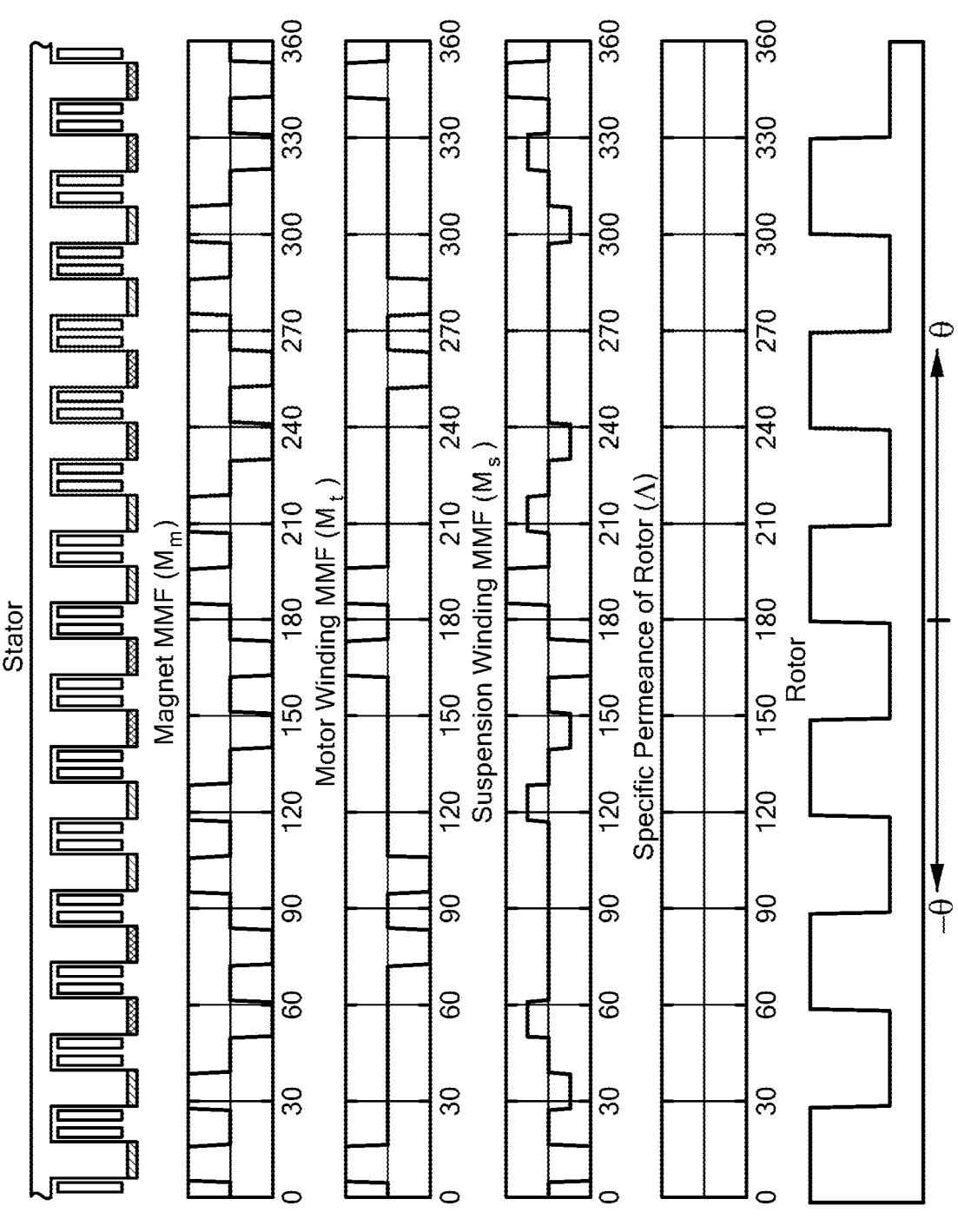
FIG. 2 is a graphical diagram showing characteristics of a symmetric stator and rotor configuration, according to some embodiments.
Figure 3:
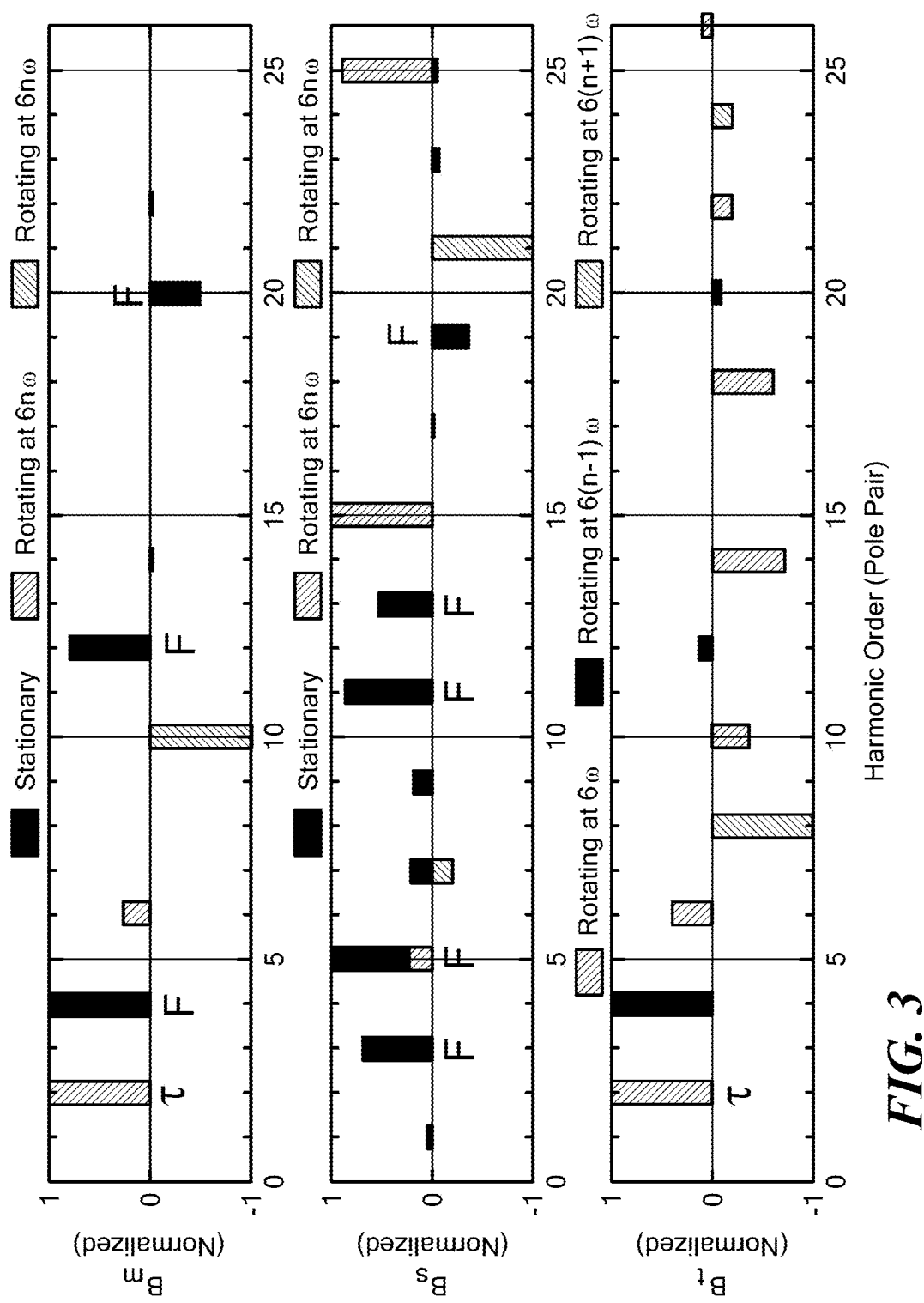
FIG. 3 shows normalized harmonic content of airgap flux densities.

Turning to FIGS. 2 and 3, with respect to force and torque generation of the proposed motor, all excitation sources are located in or on the stator. The airgap fluxes that generate force and torque are produced by modulation of all these sources by the rotor. These various airgap fluxes can be calculated as described here. The analysis considers the following assumptions:

1) Symmetrical stator and rotor geometry. Slot and teeth width are same in stator and rotor.
2) Magnet width is same as the stator teeth.
3) Ideal reluctance variation of rotor teeth (without fringing).

Various excitation MMFs are shown in FIG. 2. The specific permeance of the rotor which causes modulation is also shown in FIG. 2.

The rotor specific permeance shown in FIG. 2 can be formulated as a Fourier series:

$$\Lambda = \Lambda_0 + \Sigma \Lambda_n \sin(nZ_r(\theta - \omega t))\Lambda_0 = \Lambda_p/2; \Lambda_n = 2\Lambda_p/(n\pi Z_r), n \in \text{odd}$$

$$\Lambda = \Lambda_0 + \Sigma \Lambda_n \sin(nZ_r(\theta - \omega t))\Lambda_0 = \Lambda_p/2; \Lambda_n = 2\Lambda_p/(n\pi Z_r), n \in \text{odd}, \quad (1)$$

where $\Lambda_0$ is the average value, $\Lambda_n$ is the peak value of nth harmonic, $\Lambda_p$ is the peak value of specific permeance, $Z_r$ is the number of rotor pole/teeth, $\omega$ is the rotor rotation speed and $\theta$ is the spatial airgap angle.

The PM MMF can be represented as $$M_m = \sum_n M_{mn}\sin\left(\frac{nZ_s\theta}{4}\right)$$

$$M_{mn} = \frac{8M}{n\pi Z_s}\sum_{i=1}^{4}(-1)^{i+1}\cos\left(\frac{(2i-1)n\pi}{8}\right),$$

where $Z_s$ is the number of stator teeth and M is the peak of PM MMF.

The airgap flux density due to magnets is calculated by taking the product of MMF and specific permeance. Airgap flux density after substituting values for $Z_s=16$ and $Z_r=6$ is $$B_m = M_m \cdot \Lambda = \sum_n M_{mn}\Lambda_0\sin(4n\theta) + \quad (2)$$

$$\sum_n 0.5M_{mn}\Lambda_n[\cos(-2n\theta + 6n\omega t) - \cos(10n\theta - 6n\omega t)]$$

The airgap flux density due to the PM has three terms, the first term depends only on spatial angle and is stationary even with rotor rotation, while the remaining two terms are rotating in opposite directions to each other with rotating rotor. A normalized harmonic spectrum of $B_m$ is shown in FIG. 3. It shows the harmonic order and rotational speeds of various harmonics.

The airgap flux density generated by the motor winding with assigned two phase current excitation is calculated as follows. The motor winding MMF with both phases excited as shown in FIG. 2.

$$M_t = \sum_n (M_{tan} \cdot NI_a \cdot \cos(np\theta) - M_{tbn} \cdot NI_b \cdot \sin(np\theta))$$

$$M_{tn} =$$

$$M_{tan} = M_{tbn} = \frac{2}{np}(-\sin(np\phi) + \sin(3np\phi) + \sin(13np\phi) - \sin(15np\phi)),$$

$$NI_a = I_m\cos(6\omega t); NI_b = -I_m\sin(6\omega t),$$

$$M_t = \sum_n M_{tn}I_m\cos(-np\theta + 6\omega t),$$

where p=2 is the motor winding pole pair, $I_m$ is the peak MMF value obtained from the current commutation and $\phi = \pi/32$ is a constant. The currents are assigned to the winding based on the flux-oriented control.

Similarly, the airgap flux density by the motor winding is calculated by $$B_t = M_t \cdot \Lambda = \sum_n M_{tn}I_m\Lambda_0\cos(-np\theta - t(n+1)\omega t) + \quad (3)$$

$$\sum_n 0.5M_{mn}I_M\Lambda_n[\sin(8n\theta - 6(n+1)\omega t) - \sin(-4n\theta - 6(n-1)\omega t)]$$

The motor flux density also has three components, the first one features odd harmonics of winding pole pair (p=2) rotating at synchronous speed to the rotor ($6\omega$ is its electrical frequency). The other two compose higher order harmonics rotating at non-synchronous speeds. The torque is generated by the interaction of the second harmonic of magnet flux and second harmonic of motor winding flux, both of which have same speed. A 90° phase shift will be attained between these two fluxes by flux-oriented control to generate maximum torque. The phase of these two fluxes in equations (2) and (3) are the same due to motor MMF for this analysis. In actual operation, the specified motor currents, as shown in FIG. 2, will be applied when the rotor is shifted by 15° (90° electrical).

The suspension winding MMF of one axis and corresponding airgap flux density is calculated as $$M_s = \sum_n M_{sn}\sin(n\theta)$$

$$M_{sn} = \frac{2NI_s}{n}[\cos(n\phi) - \cos(3n\phi) + \cos(29n\phi) - \cos(31np\phi) +$$

$$0.5(\cos(5n\phi) - \cos(7n\phi) - \cos(9n\phi) + \cos(11n\phi) - \cos(21n\phi) + \cos(23n\phi))],$$

where $NI_s$ is the peak value of suspension winding MMF and $\phi = \pi/32$ is a constant.

$$B_s = M_s \cdot \Lambda = \sum_n M_{sn} \Lambda_0 \sin(n\theta\omega t) + \qquad (4)$$

$$\sum_n 0.5 M_{sn} \Lambda_n [\cos(-5n\theta + 6n\omega t) - \cos(7n\theta - 6n\omega t)]$$

The suspension airgap flux also features three components; one is stationary and only depend on the spatial coordinate and the other two are rotating. These stationary fluxes allow this motor to generate suspension force independent of the rotor orientation. There are magnet flux density harmonics at n=4, 12, 20. Therefore suspension winding flux densities of n±1 stationary harmonics are required to generate force. All these stationary harmonic components are generated by the suspension winding (FIG. 3) and these have a correct phase relation with the magnet flux density as well. The phase relation defines the direction of force generated and having coherent phase generates unidirectional forces.

The above analysis can be used to vary the expected force and torque behavior of the disclosed bearingless split-tooth flux-reversal slice motor topology. The method also demonstrates that the torque generation is the same as in PM synchronous motors while the force generation utilizes stationary harmonics.

A motor based on the topology of FIG. 1C may have the following specifications: 100 mNm motor torque, 3000 rpm, 50 N radial force to center the rotor, 2.5 mNm (peak) cogging torque and 5.4 N/mm of passive axial stiffness. The rotor diameter and axial length may be fixed by an impeller and pump housing. Thus, for example, rotor 142 may have an outer diameter of about 50 mm and axial height of about 10 mm. The stator 146 width may be about 170 mm.

With the disclosed motor topology, cogging torque can be reduced by keeping the stator such that all the teeth are uniformly distributed, and the slots have same dimensions. Although a non-uniformly spaced stator teeth may have least cogging torque, in that case the slot areas will be different, and winding will be non-uniform. Cogging torque can be minimized using other modifications such as extending the permanent magnets 150 on both sides of stator teeth 148 by using magnets wider than the stator teeth as shown in FIG. 1C. This helps in reducing the cogging torque and increases the force and torque capabilities slightly.

Figure 4:
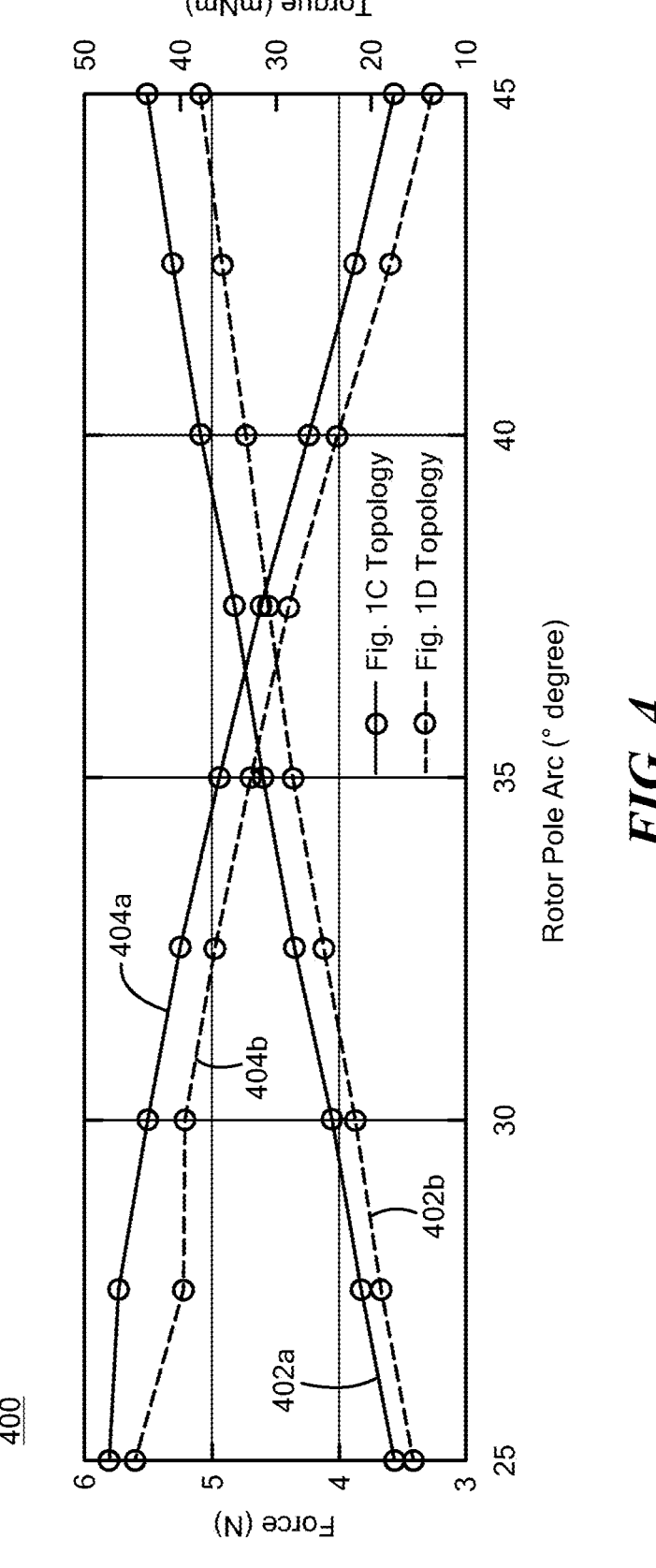
FIG. 4 shows rotor pole arc sensitivity on force and torque generation for two different-tooth flux-reversal motor topologies.

The dimensions of rotor 142 may be important since it modulates the flux and affects the torque and force production. To that extent, a relatively smaller rotor pole arc length allows larger torque since the reluctance variation will be large and a larger rotor pole arc length allows larger force since the area will be large. For bearingless motors, a balance between force and torque is desired. Therefore the sensitivity of rotor pole arc may be obtained using finite element (FE) simulation, such as shown in FIG. 4. The contrasting behavior of force and torque is clear and a rotor pole of 35° is selected considering the current rating and the peak force/torque requirements.

Referring briefly to FIG. 4, a graph 400 shows rotor pole arc sensitivity on force and toque generation for the split-tooth flux-reversal motor topology of FIG. 1C, where the magnets are covering whole airgap and, and of FIG. 1D, where magnets are arranged to accommodate optical sensors. Curves 402a and 402b correspond to force, whereas curves 404a and 404b correspond to torque.

Figure 5A:
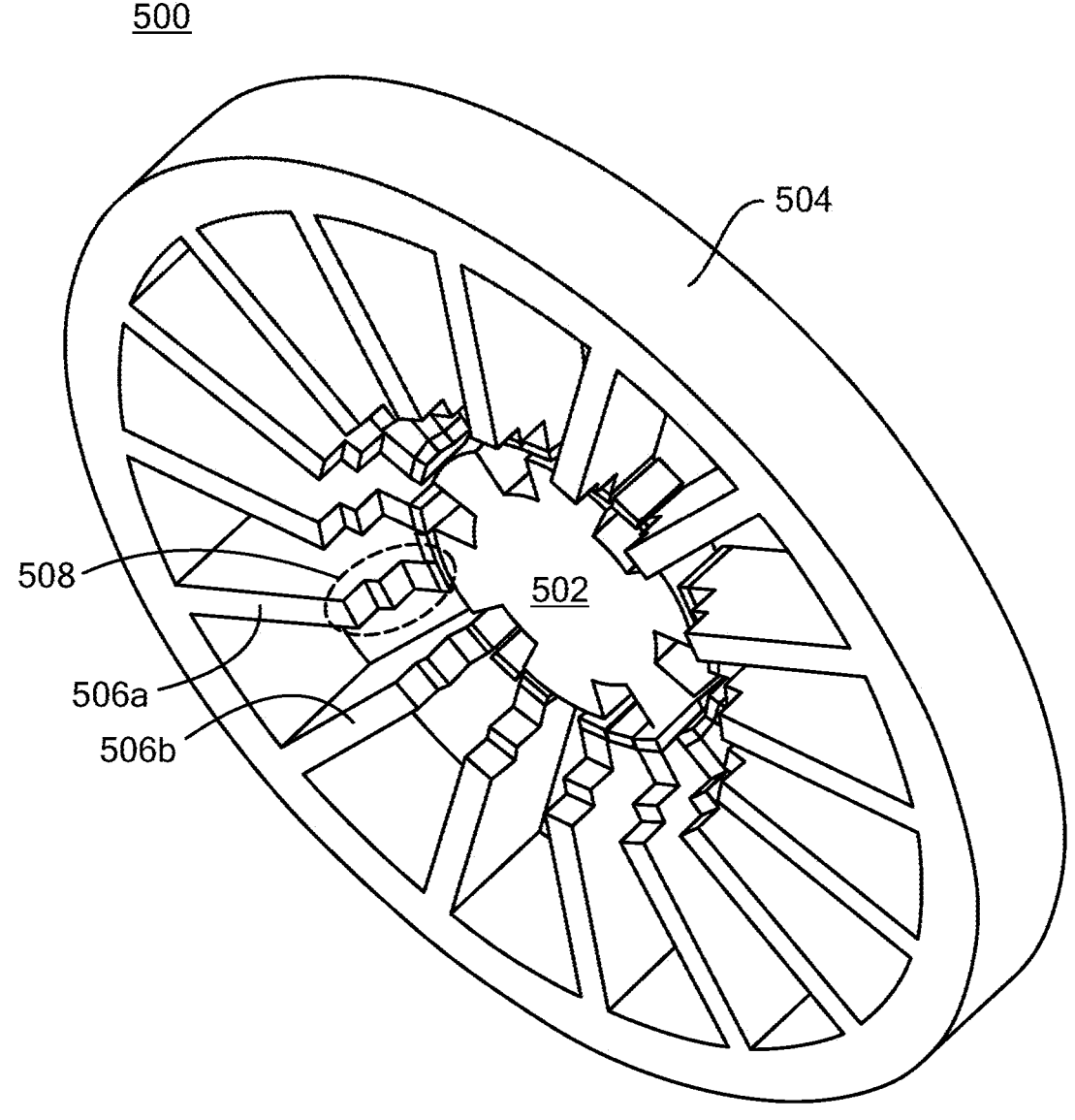
FIG. 5A is a perspective review of a split-tooth flux-reversal motor showing an example of stator teeth design, according to some embodiments.

Turning to FIG. 5A, an illustrative split-tooth flux-reversal motor 500 includes a rotor 502 and a stator 504 having a plurality of teeth 506a, 506b, etc. (506 generally). The stator teeth coil windings are omitted from FIG. 5A for clarity. It is appreciated herein that a larger stator slot area may be required to accommodate the levitation and motor ampere-turns. Longer stator teeth can cause a large leakage flux. The volume of the tooth away from the airgap will have larger flux since flux in the slot and airgap circulates via back iron. Hence the backward portion of the stator teeth can have accumulated flux. Thus, in some embodiments, the area of the stator teeth 506 can be increased away from the airgap in stepped formation as shown in FIG. 5A (e.g., in the region 508 for tooth 506a). However, since the stator teeth are close to each other near airgap, the flux leakage between teeth is dominant there. Therefore, the azimuthal overlapping area of stator teeth close to the airgap may be kept small to avoid excessive flux leakage.

The 3-step design illustrated in FIG. 5A can reduce the area where the teeth 506 are close to each other, but has large area where teeth are far from each other. This can reduce the leakage close to airgap and provide enough area for flux away from the airgap.

Figure 5B:
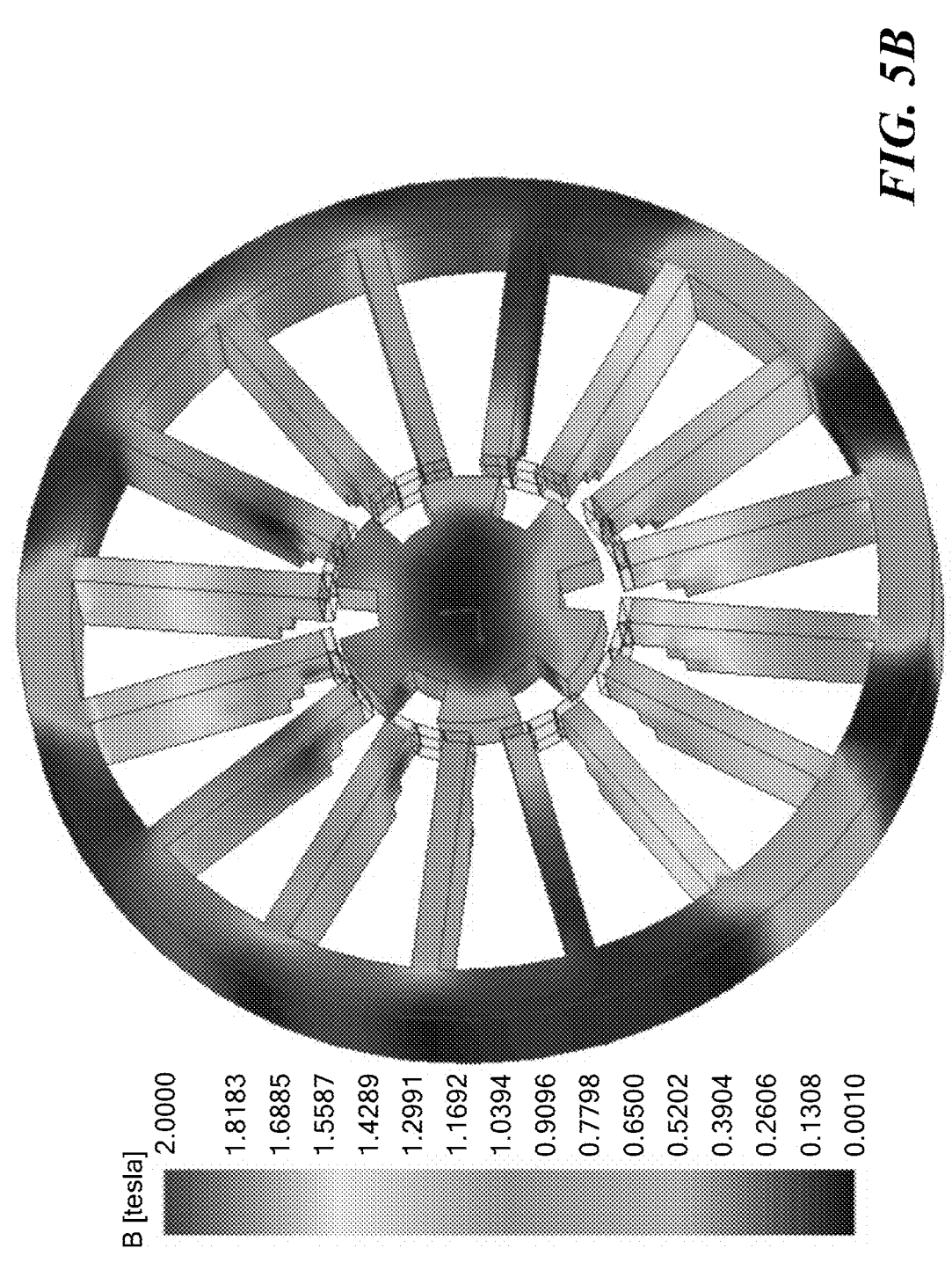
FIG. 5B illustrates design verification under operation for a stator of a split-tooth flux-reversal motor, according to some embodiments.

FIG. 5B shows flux density that may be achieved during operation (e.g., maximum current operation) of a split-tooth flux-reversal motor topology according to the present disclosure. In particular, shown is flux density during the lift off condition with $I_x$=1000 AT to move the rotor from 1.2 mm shifted from center to the center. The flux density is approximately at the knee point of the steel showing a good utilization of stator steel.

This operation is the rotor take off during initialization of levitation when the rotor has to overcome the attraction from the stator and attain the center position. With the pump assembly, the rotor will be shifted by 1.2 mm from center initially and an MMF of 800 AT is required to centre the rotor. The flux density in the stator with the take off MMF with some margin (1000 AT in X axis) is shown in FIG. 5B. The M15 29 Gauge electrical steel may be used for the stator and rotor construction, which has a saturation point of about 2T. The flux density in FIG. 5B is close to the saturation flux density and the flux density distribution in each tooth verifies the requirement of larger stator teeth area away from the airgap.

In some cases (e.g., blood pump applications), a coil winding design may be used that reduces and ideally minimizes losses to avoid heating. Various winding optimizations and further measures like heat sink can also be used. In some cases, a continuous motor specification of 100 mNm (200 AT RMS) and 4 N (approximately 0.2 mm shift, 100 AT DC) may be provided for, which may give an approximately 300 AT total by algebraic summation. A 3 A/mm² current density may be chosen for natural cooling, as may a 60% slot fill factor giving 166 mm² of coil area. In some embodiments, the dimensions of the coils can be selected such that the coil can be slid on the stator teeth. A coil with 300 turns of 22 AWG wire may satisfy this coil area. The switching amplifier DC voltage requirement can be calculated with this winding design. With 300 turns, each coil has a peak inductance of 15 mH, with a small back EMF in each coil and a maximum speed of 3000 rpm (300 Hz, 12 pole motor), the voltage required to drive 0.66 A RMS (200 AT/300T) current is 26 V peak. Moreover, the initial take off current of 3.3 A (1000 AT) sets the peak current requirement of amplifier. In some cases, these ratings can be achieved using inverters for 48 V systems. Further considering an 80% packing factor of the coils, the total ohmic loss for 0.66 $A_{rms}$ may be 4 W (0.25 W each coil).

Figure 6A:
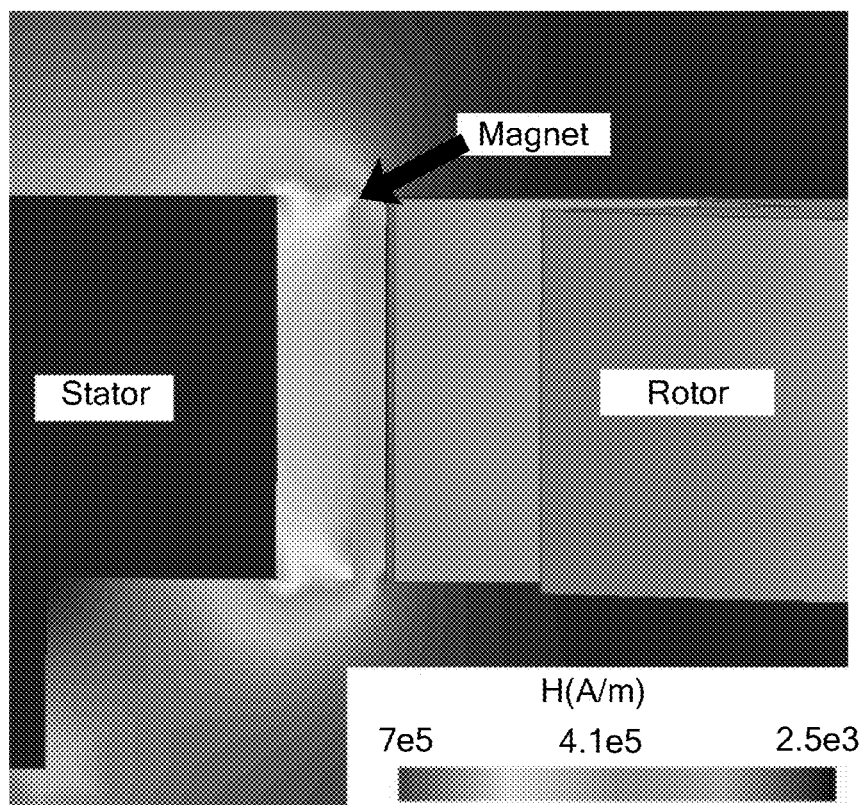
FIGS. 6A and 6B show magnetization force in permanent magnets of a split-tooth flux-reversal motor under rotor lift off conditions, according to some embodiments.
Figure 6B:
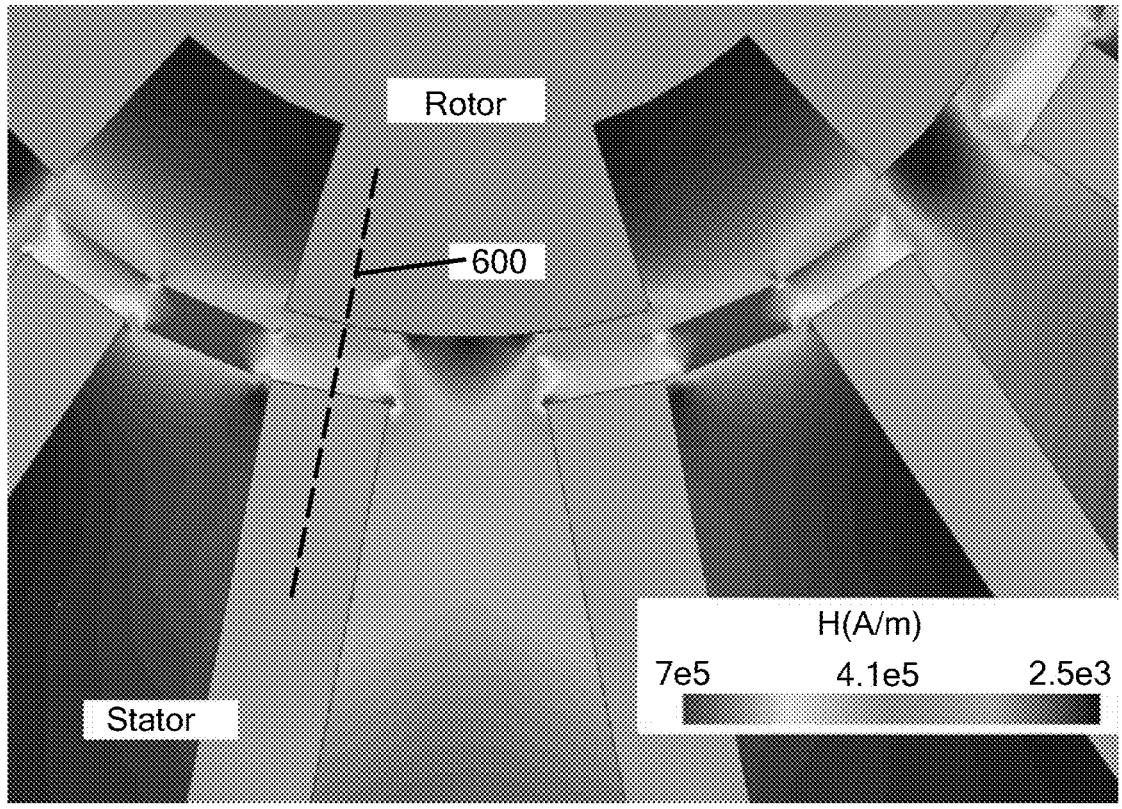

Turning to FIGS. 6A and 6B, according to some embodiments, a split-tooth flux-reversal motor can include permanent magnets that are connected directly in series with the winding. During extreme operations, there may be a concern of demagnetization. NdFEB N45 magnets have coercivity of approximately 950 kA/m and do not demagnetize when put in air. This means the magnets will not demagnetize if the demagnetization force is away from this coercivity value. The demagnetization of the magnets can be evaluated for the peak operating condition mentioned above.

FIGS. 6A and 6B show the magnetization force (H) in the magnets under rotor lift off conditions with 1000 AT and 1.2 mm shifted rotor, with FIG. 6A corresponding to a cross section of FIG. 6B, taken at dotted line 600. As seen from FIG. 6A, demagnetization force (−H) in the magnet is less than 700 kA/m, when the rotor pole is aligned to magnet. FIG. 6B shows demagnetization force (−H) on the magnets at various locations. −H for the all the magnets in both cases is in the safe operating range for temperature <40° C. As shown in FIG. 6B, the magnets in between the stator teeth may appear heavily demagnetized even though there is no direct winding flux since it is in air and not in magnetic circuit. The magnets overlapping with the rotor pole can have reasonable demagnetization force even with 1000 AT winding MMF injected against the magnet flux. Thus, it is shown that a disclosed split-tooth flux-reversal motor may be safe from demagnetization during startup.

Figure 7:
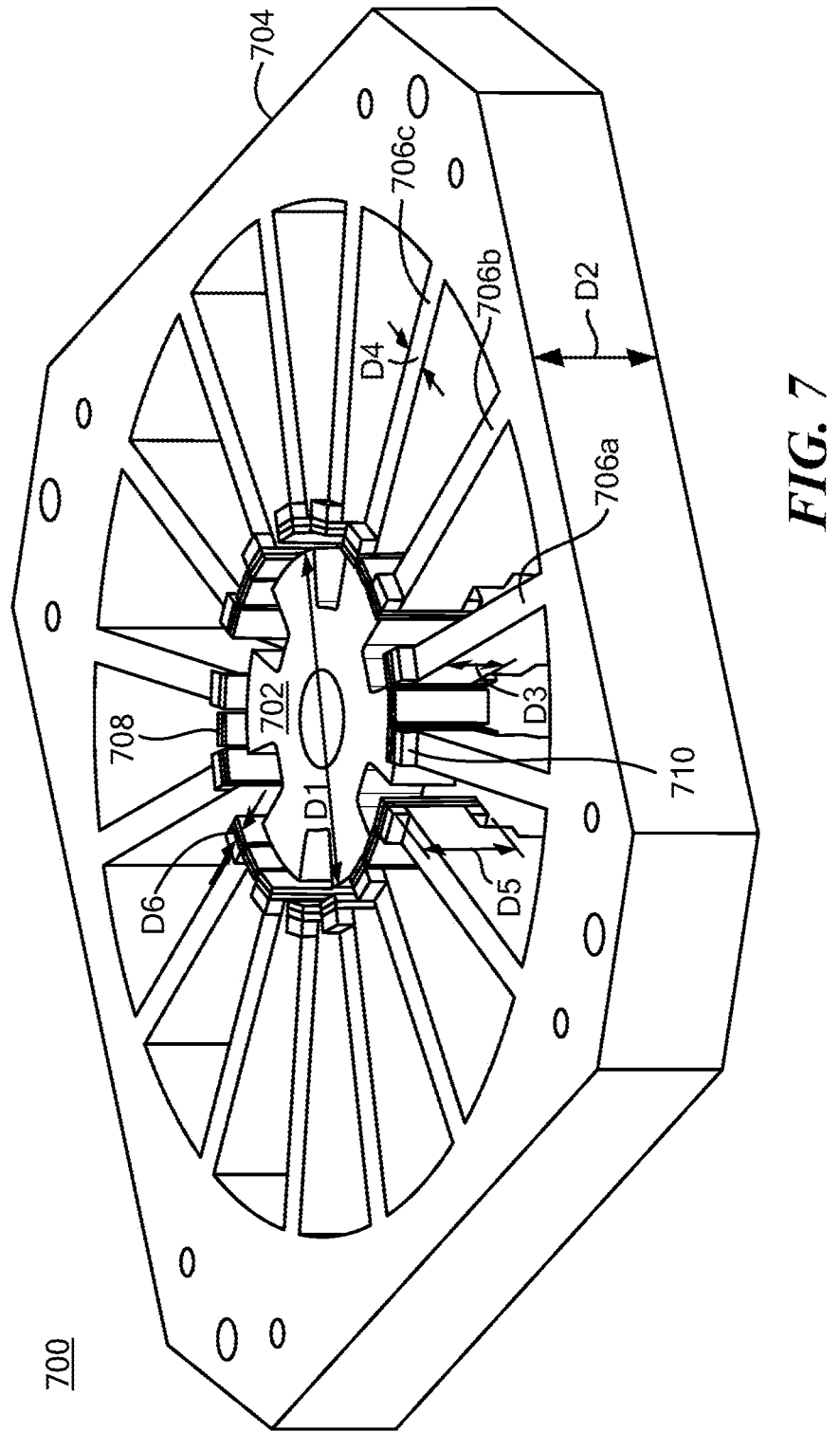
FIG. 7 is a perspective view of a split-tooth flux-reversal motor topology with increased magnet lengths, according to some embodiments.

Turning to FIG. 7, according to some embodiments, a split-tooth flux-reversal motor topology can utilize increased magnet lengths to enhance the passive magnetic stiffness. Illustrative motor topology 700 includes a rotor 702 and a stator 704 that may be separated by an air gap. Stator 704 can have a plurality of split teeth 706a, 706b, 706c, etc. (706 generally). Rotor 702 has an outer diameter D1. Stator 704 can have a thickness D2, with the height of each stator tooth 706 decreasing from about D2 to D3 toward the airgap in stepped formation. Stator teeth 706 can have a width D4. In some cases, rotor 702 can have a height substantially equal to D3.

Magnets 708 may be attached at the ends of the stator teeth 706, and additional magnets may be positioned between some pairs of stator teeth, as shown. Magnets 708 may each have a length D5 and a thickness D6, where the magnet thickness can be achieved by stacking two commercially available magnets, also as shown. Magnets 708 may be longer than the height of the stator teeth 706 where they are attached. That is, D5 may be greater than D3. Steel pieces 710 may be provided on top and bottom surfaces of each stator tooth 706 to provide backing for the longer magnets.

In some examples, the air gap may be about 2 mm, D1 may be about 50 mm, D2 may be about 20 mm, D3 may be about 10 mm, D4 may be about 5 mm, D5 may be about 15 mm, and/or D6 may be about 2 mm.

In disclosed motor topologies, when the rotor displaces in the axial direction, the PM flux at the non-overlapping stator/rotor peripheral area in the airgap leaks back to the stator instead of crossing the airgap. This phenomenon makes tilt and axial stiffness very small, which makes pump operation hardly feasible. A fix by keeping the same stator and rotor is found where the length of magnets is increased (e.g., from 10 mm to 15 mm) with small pieces of steel 710 yokes as shown in FIG. 7. In some cases, a magnet length of 15 mm may be selected due to the magnet availability off-the-shelf. This arrangement imitates a stator longer than the rotor and this extra magnet volume creates the leakage flux. Therefore with an axial or tilt motion, the restoring flux crossing the airgap is still available and the leakage to the stator is fed by extra magnet volume.

Next described is a levitation and speed control architecture, control system design and parameter identification for a split-tooth flux-reversal motor.

Figure 9:
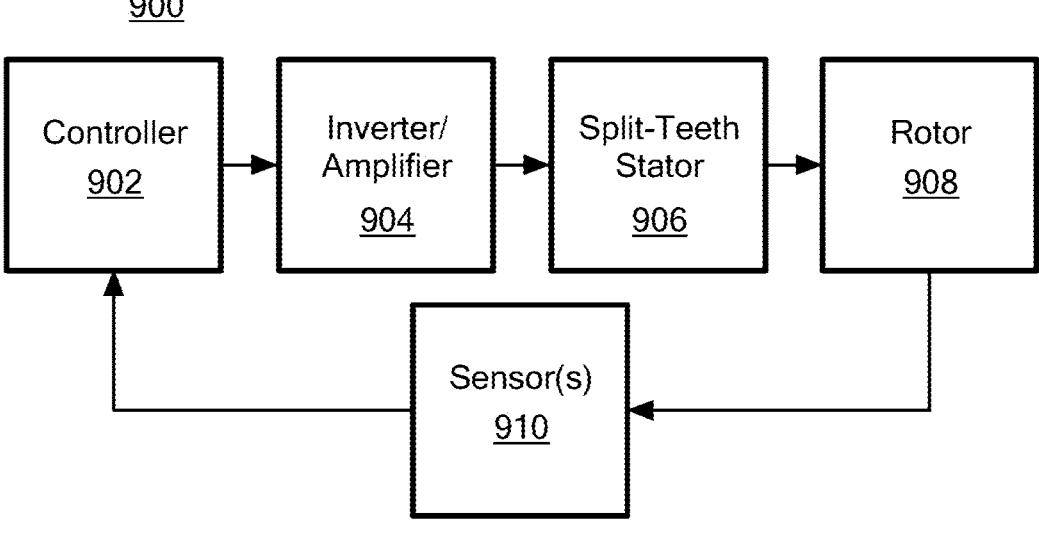
FIG. 9 shows an example of a motor system in which a split-tooth topology may be employed, according to some embodiments.

FIG. 9 shows an example of a motor system 900 in which a split-tooth topology may be employed, according to some embodiments. Illustrative system 900 includes a controller 902, one or more inverters/amplifiers 904, stator 906, rotor 908, and one or more sensors 910. Stator 906 and rotor 908 may be provided having any of the split-tooth flux-reversal motor topologies disclosed herein. Controller 902 can generate one or more control signals (e.g., levitation/suspension control signals and/or speed control signals) to excite the coils of stator 906. In turn, stator 906 can generate flux to turn rotor 908. The one or more sensors 910 can detect position of the rotor 908 and provide such position information as feedback to controller 902. Controller 902 can include electronic circuitry (digital and/or analog) configured to perform any or all of the motor control techniques described below. Inverters/amplifiers 904 may include one or more switching amplifiers, as discussed below.

A magnetically levitated slice rotor can be modeled as a spring mass system with negative spring stiffness. Parameter estimates obtained from FE simulations can provide an initial plant model for controller design. Once the rotor is levitated, the experimental frequency responses of the plant and return ratio can be obtained and the actual parameters can be identified from these frequency responses. Table 1 shows examples of such estimated motor parameters. It also shows the position sensor gains obtained experimentally. The developed sensor gains depend on the distance from the rotor, which may vary across different deployments.

Figure 8:
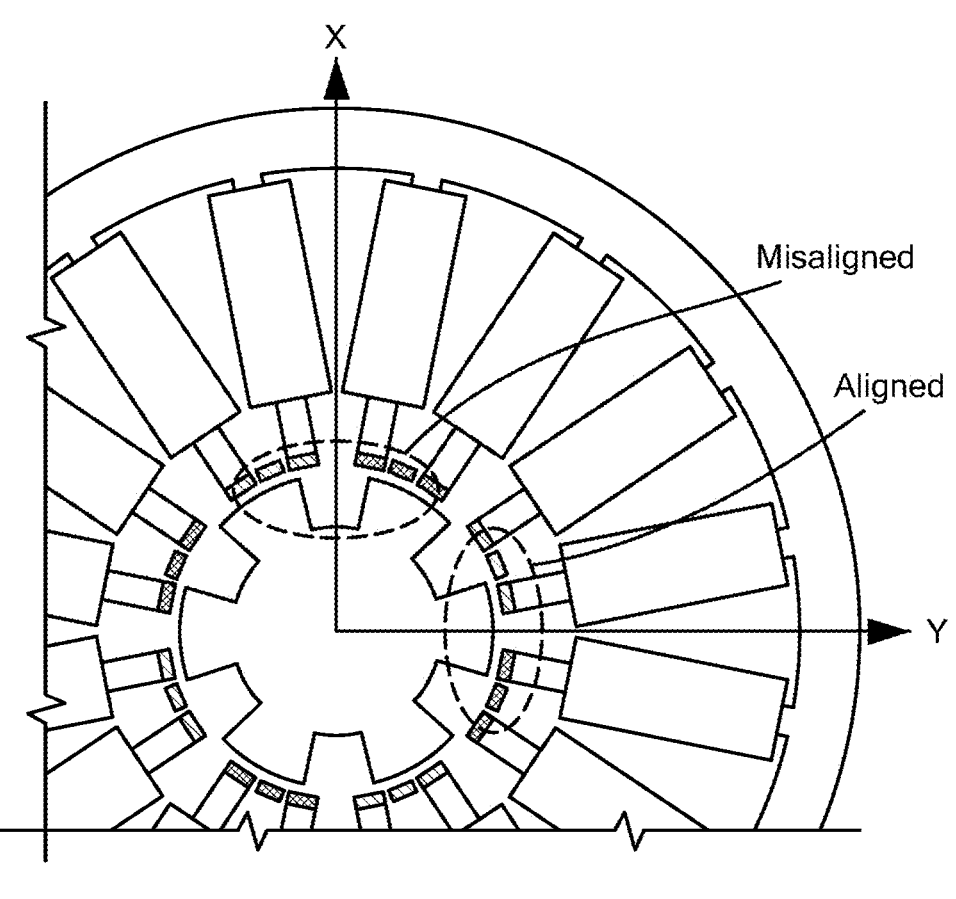
FIG. 8 shows rotor orientations that may be used for control and design purposes, according to some embodiments.

The salient pole rotor can cause variable magnetic stiffness as well as some parasitic variation in force constant at different rotor orientations. The definition of these variations is based on the rotor orientation with the X-Y axes, along which the independent forces are generated. Therefore, two specific rotor orientations may be considered for control design, one is the rotor pole aligned with X or Y axis and the other is a misaligned pole as shown in FIG. 8. FIG. 8 shows rotor orientations for control and design purposes. The levitation axes are defined between the teeth, hence the important rotor orientations are when the rotor pole is directly aligned to any of the axes or completely misaligned. The magnetic stiffness and force constant values may be obtained from FE simulations as shown in Table 1.

Figure 10:
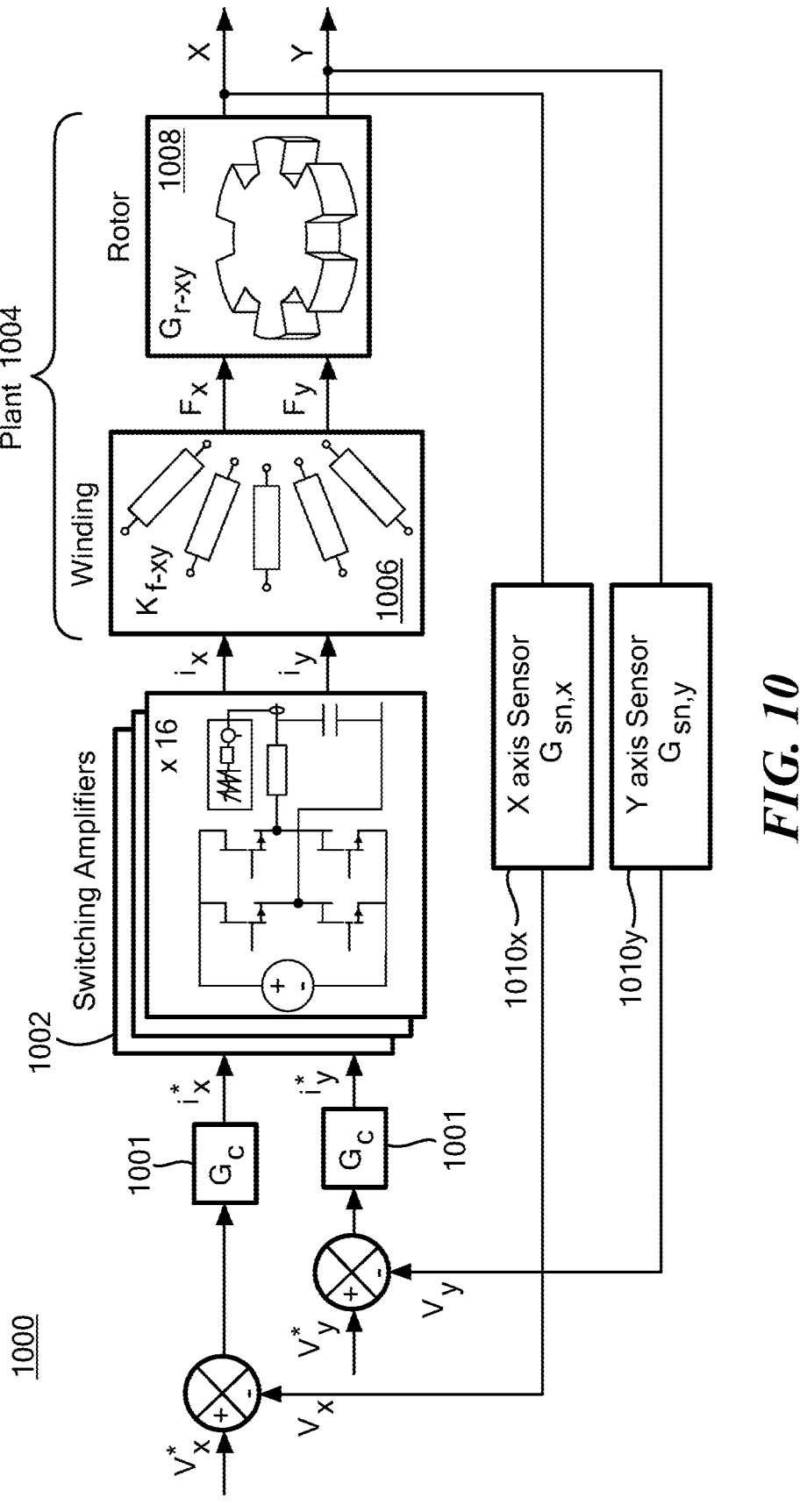
FIG. 10 shows levitation position control that may be utilized within a split-tooth flux-reversal motor system, according to some embodiments.

FIG. 10 shows levitation position control that may be utilized within a split-tooth flux-reversal motor system, according to some embodiments. Illustrative system 1000 includes a suspension controller 1001 represented by blocks $G_c$, switching amplifiers 1002, a plant 1004 comprising a stator 1006 and rotor 1008, and position sensors 1010x, 1010y (1010 generally). X and Y force generation is decoupled and hence the control is decoupled. $I_{XY}$ is distributed according to the commutation law and given as current reference to the amplifiers.

The plant 1004 as specified in FIG. 10 can be written as $$G_{p-xy} = K_{f-xy}G_{r-xy} = \frac{K_{f-xy}}{ms^2 - K_{s-xy}}$$

As mentioned earlier, some parameters are fixed along X-Y axes whereas other depends on the rotor orientation. $G_{p-xy}$ are X and Y plant transfer function, $K_{f-xy}$ is the force constant $(N/A_{rms})$ in X and Y direction but the variation along aligned and misaligned axes is considered as well for control design, m is the mass of the rotor, $K_{s\_xy}$ is the negative stiffness (N/m) in X and Y direction and similarly the variation along aligned and misaligned axes is considered here as well. A position sensor 1010 can have synchronous demodulation-based signal processing whose bandwidth is defined by the low pass filter in the algorithm. Thus a sensor 1010 can be modeled as $$G_{sn-xy} = K_{sn-xy} G_{LPF} = K_{sn-xy} \times \frac{\omega_f^2}{s^2 + 2\zeta_f \omega_f s + \omega_f^2}$$

where $K_{sn-xy}$ is the sensor gain along X-Y axes, since the sensor is aligned and fixed with X-Y axis. The sensor gain values are shown in Table 1. The low pass filter parameter values are $\zeta_f = 0.707$ and $\omega_f = 211000$ rad/sec.

A suspension control loop, such as illustrated in FIG. 10, can be designed using a lead controller and a first order filter using a second order pole structure. Having a second order pole helps to control the phase drop by utilizing complex poles. Hence the phase can be maintained over a wider range. The suspension controller 1001 can also include a PI controller to provide higher gain at low frequency and to remove steady state error.

$$G_c = K_p \frac{\alpha \tau s + 1}{\frac{s^2}{\omega_0^2} + \frac{2\zeta s}{\omega_0} + 1} \cdot (1 + \frac{K_i}{s})$$

where $K_p = 0.7$, $\alpha = 10$, $\tau = 2.5 \times 10^{-4}$, $\omega_0 = 4000$, $\zeta = 0.7$, $K_i = 20$. The experimental frequency response for the return ratio can be obtained to verify the stability and bandwidth of the suspension control. The control loop can be shown to have a crossover frequency of 100 Hz and the phase margin of 30°.

Figure 11:
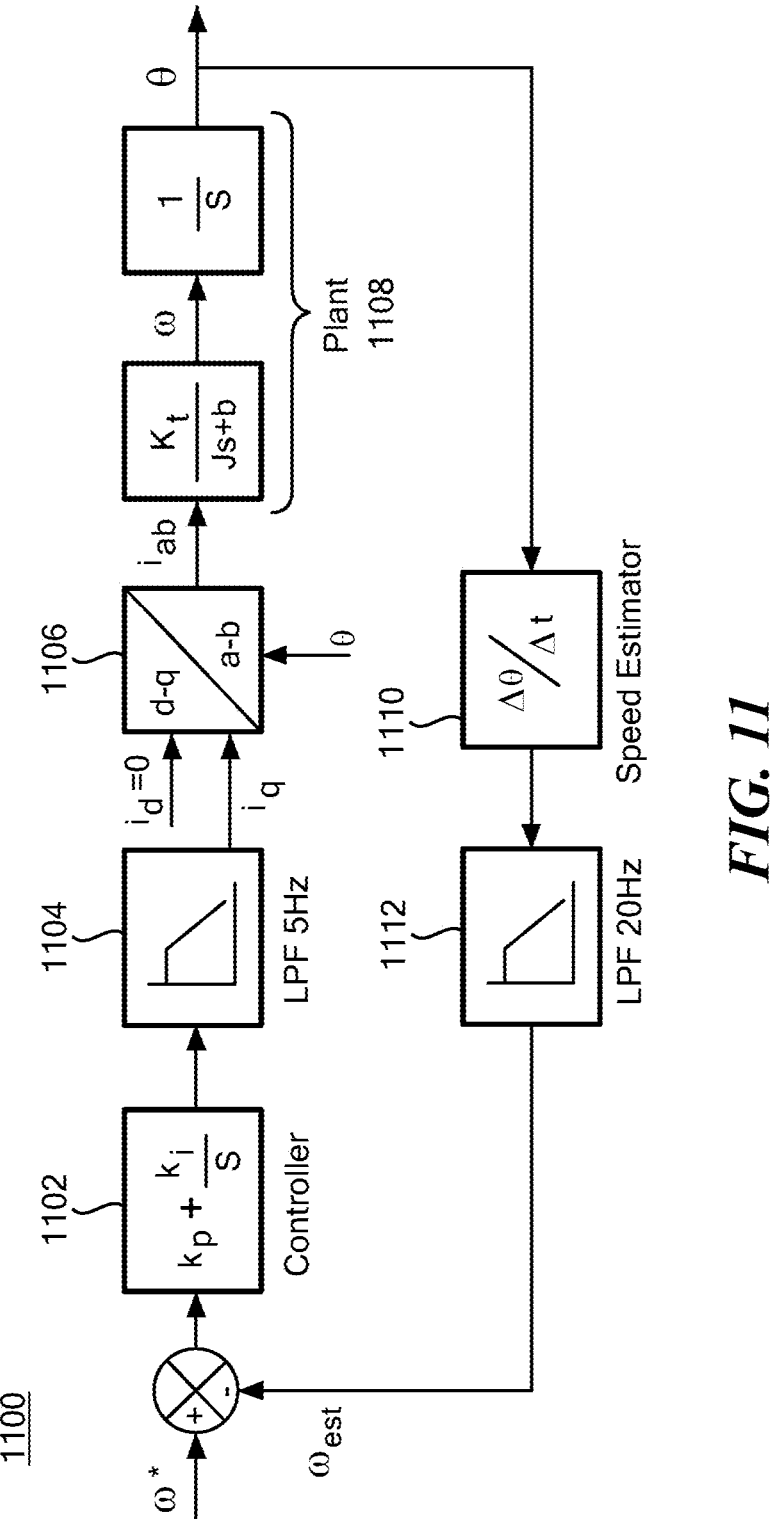
FIG. 11 shows flux-oriented motor speed control that may be utilized within a split-tooth flux-reversal motor system, according to some embodiments.

FIG. 11 shows flux-oriented motor speed control that may be utilized within a split-tooth flux-reversal motor system, according to some embodiments. Illustrative system 1100 includes a controller 1102, a low pass filter 1104, a coordinate transform 1106 (e.g., an inverse Park transformation), a plant 1108, a speed estimator 1110, and another low pass filter 1112, arranged as shown. Plant 1108 may have any of the disclosed split-tooth flux-reversal motor topologies disclosed herein. With system 1100, only q axis control may be used. Speed can be estimated using an angle sensor, for example. Of note, a switching amplifier is much faster than the speed control bandwidth, hence, it may be considered as a gain of one (1) in the control design.

The speed control of a flux-reversal motor may be similar to the vector control of conventional permanent magnet motors. In this motor, since the magnets and winding are on the stator, the rotor pole defines the d-q axis. The rotor angular position can be measured using a sensor and used for the vector control of this 12-pole motor. Only q-axis current control (torque control) is implemented as shown in FIG. 11, since the d-axis control (flux weakening) will not work for pump load. The torque constant ($K_t$) is obtained from FE simulations and the value is tweaked using experimental results. The damping coefficient (b) can be experimentally obtained from steady state speed results with varying currents and then used for speed control design. It can be shown that speed control has a crossover frequency of 2 Hz and phase margin of 40°.

TABLE 1

| Estimated Performance Parameters | | |
| --- | --- | --- |
| Parameter | Est. Value | Fitted Value |
| Aligned Radial Stiffness, $K_{sa}$ (N/mm) | −22 | −18 |
| Misaligned Radial Stiffness, $K_{sm}$ (N/mm) | −32 | −22 |
| Aligned Force Constant, $K_{fa}$ (N/A$_{rms}$) | 11.7 | 11.7 |
| Misaligned Force Constant, $K_{fm}$ (N/A$_{rms}$) | 12.9 | 12.9 |
| X Sensor Gain, $K_{snx}$ (V/mm) | 5.4 | 3.83 |
| Y Sensor Gain, $K_{sny}$ (V/mm) | 6.3 | 4.03 |
| Torque Constant, $K_t$ (mNm/A$_{peak}$) | 96.8 | 87.1 |
| Rotor mass, m (g) | 114 | — |
| Rotor Inertia (FE), J (kg m$^2$) | $3.15 \times 10^{-5}$ | — |
| Aligned Tilt Stiffness (mNm/° tilt) | −26.5 | — |
| Misaligned Tilt Stiffness (mNm/° tilt) | −30.3 | — |
| Axial Stiffness, (N/mm) | −5.4 | — |
| b (Nm/(rad/sec)) | — | $21.3 \times 10^{-6}$ |

Figure 12:
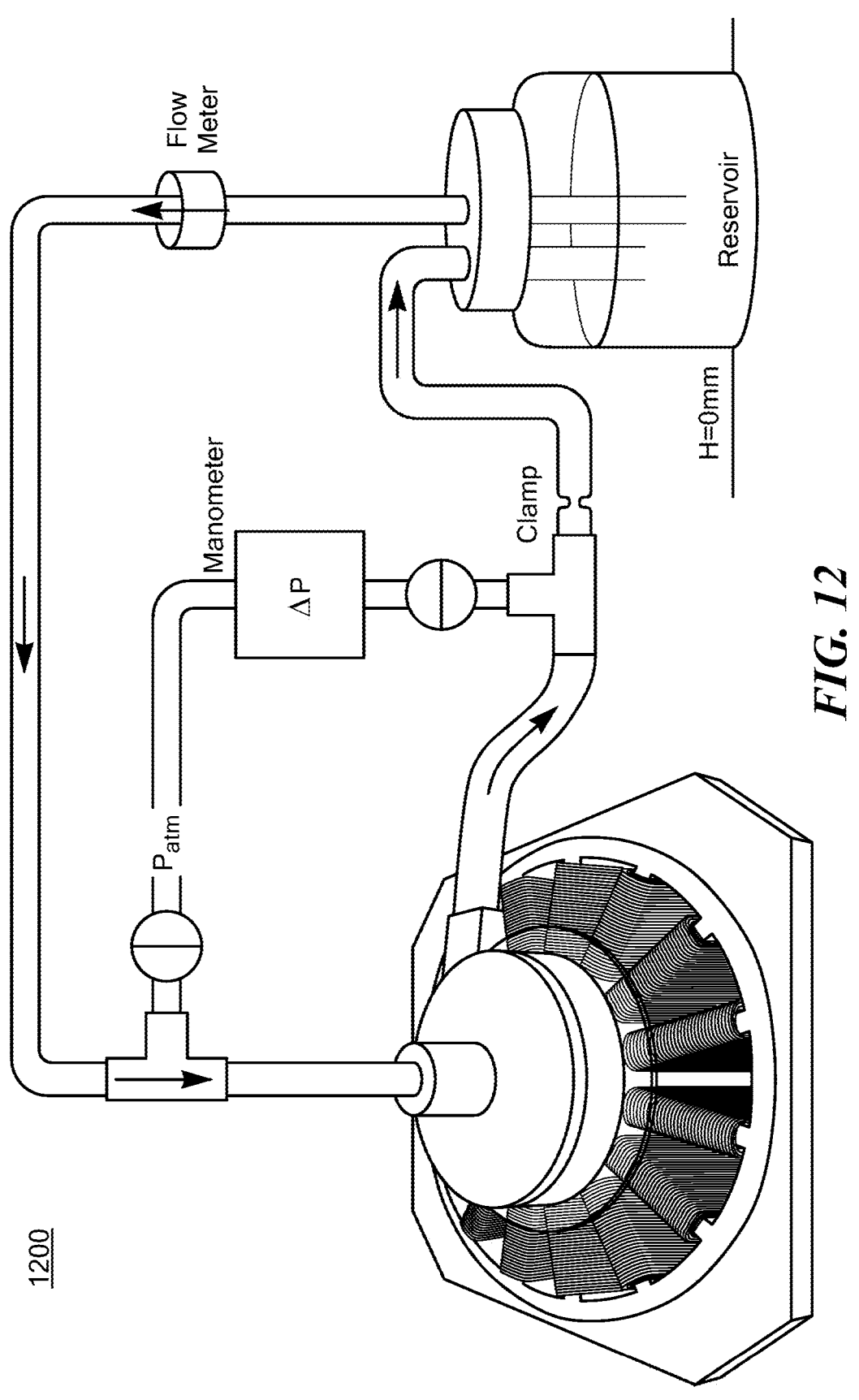
FIG. 12 shows a fluid pumping system employing a split-tooth flux-reversal motor, according to some embodiments.

FIG. 12 shows an example of a fluid pumping system 1200 employing a split-tooth flux-reversal motor, according to some embodiments. As shown, the rotor can be integrated with an impeller and pump housing in a closed fluidic circuit to test the pump. The flow and outlet pressure can be measured while varying the outlet restriction and running the pump at several speeds to verify the successful operation of the motor integrated with a pump. The output pressure can be controlled using a Hoffman clamp at the outlet.

Figure 13:
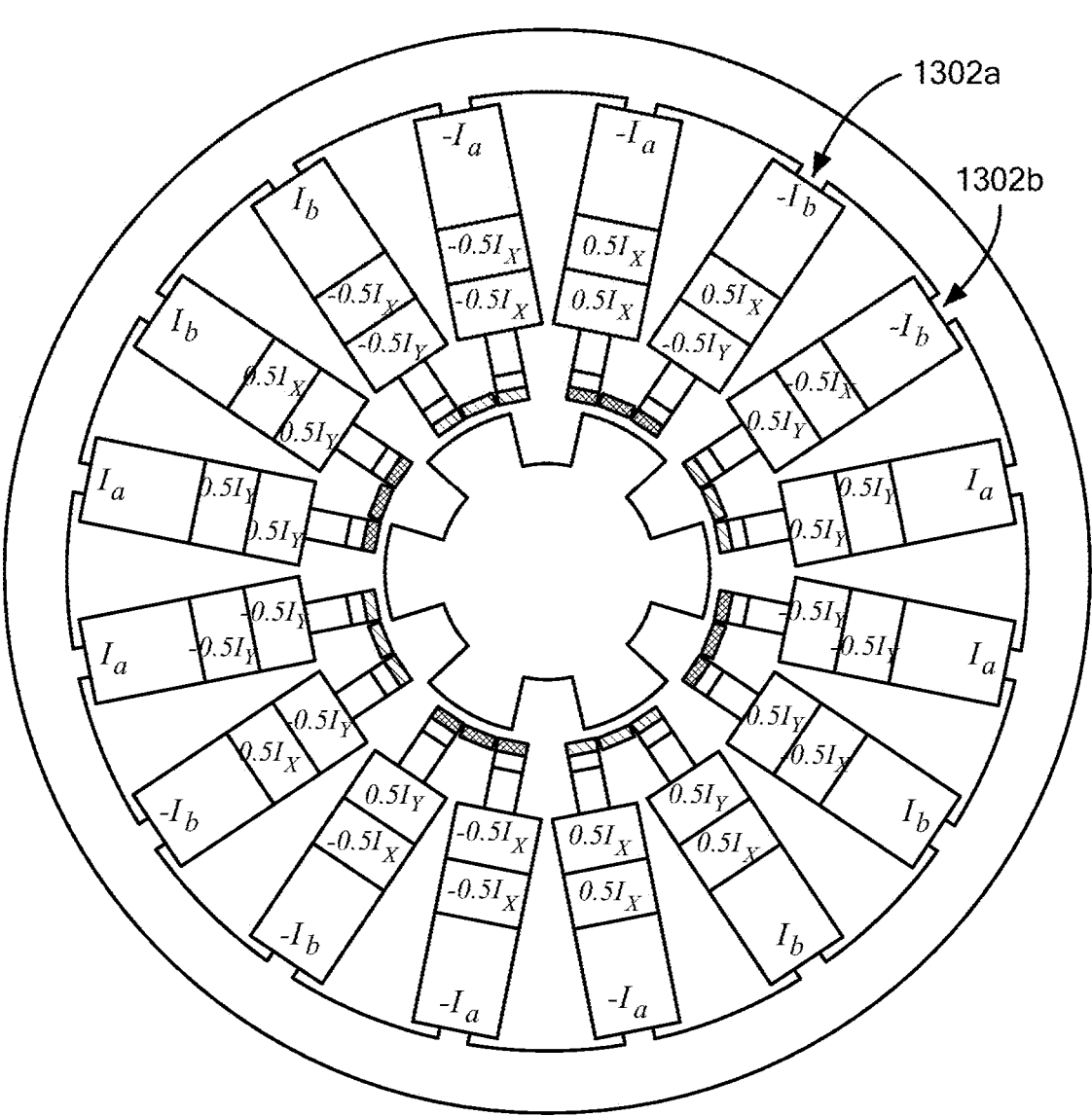
FIG. 13 shows an example of a split-tooth flux reversal motor topology with separate windings for motor and levitation operation, according to some embodiments.

FIG. 13 illustrates a split-tooth flux reversal motor topology 1300 with separate windings for motor and levitation operation, according to some embodiments. As shown, each of the stator teeth 1302a, 1302b, etc. (1302 generally) can be wound with multiple coils denoted $I_a/I_b$, $I_x$, and $I_y$ with each of the coils denoted $I_a$, $I_b$, $I_x$, and $I_y$ can be connected in series. The winding stack on each tooth 1302 can be changed depending on the amplifier ratings. It is appreciated that windings farther from the rotor-stator airgap may have more leakage and thus may be operated using larger current.

Figure 14:
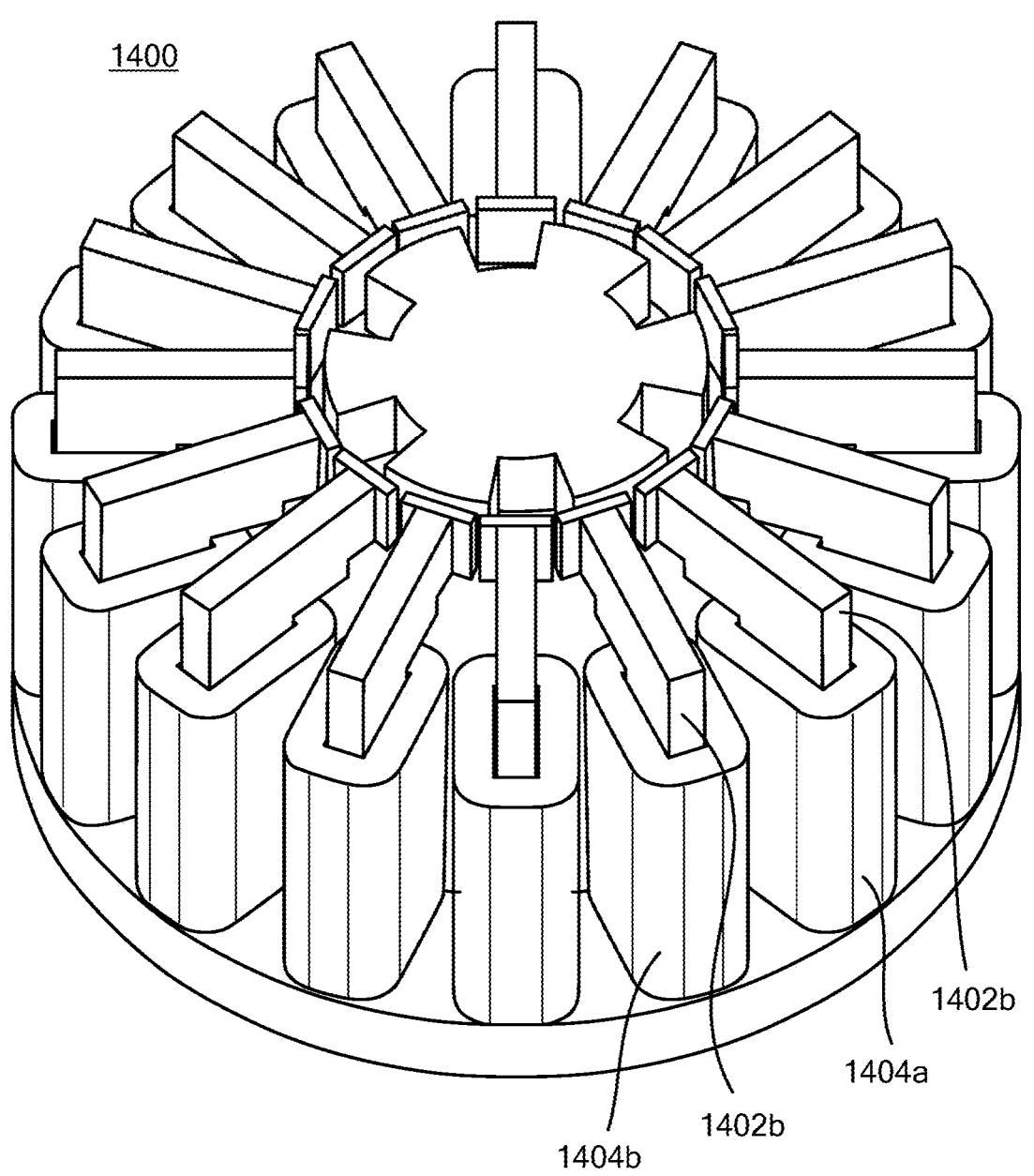
FIG. 14 shows a split-tooth flux reversal motor with a temple stator, tooth flux reversal motor topology with separate windings for motor and levitation operation, according to some embodiments.

FIG. 14 shows a split-tooth flux reversal motor 1400 with a temple stator design. As shown, stator teeth 1402a, 1402b, etc. (1402 generally) are elevated (i.e., longer) such that a significant portion of the teeth 1402 are parallel to each other, providing a large overlapping area for leakage flux. It is appreciated herein that the dimensions of coils 1404a, 1404b, etc. are critical to flux leakage.

Figure 15:
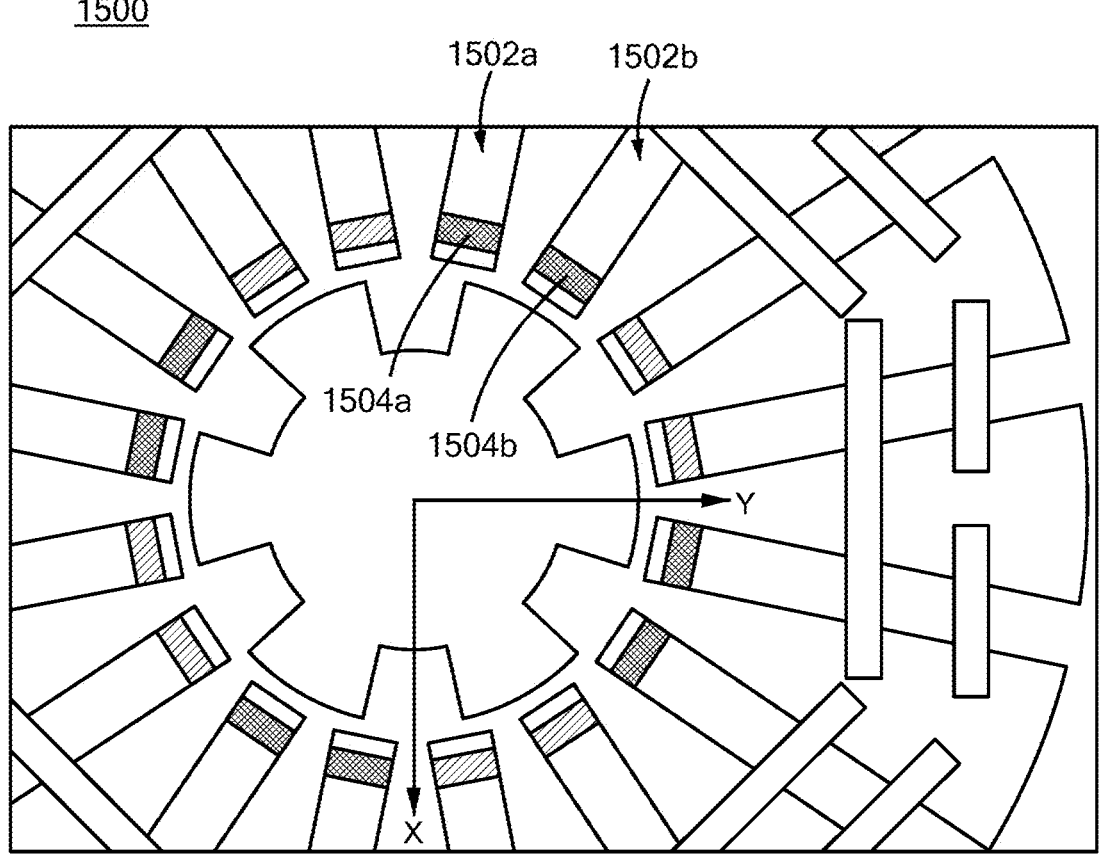
FIG. 15 shows a split-tooth flux reversal motor topology with magnets buried inside the stator teeth iron, according to some embodiments.

FIG. 15 shows a split-tooth flux reversal motor topology 1500 with magnets 1504a, 1504b, etc. (1504) buried inside respective ones of stator teeth 1502a, 1502b, etc. (1502 generally). Ins some embodiments, stator teeth 1502 may be formed out of iron and magnets may be buried within recess formed therein. In other embodiments, the stator, magnet, and an iron piece may be glued together.

As used herein, the terms "processor" and "controller" are used to describe electronic circuitry that performs a function, an operation, or a sequence of operations. The function, operation, or sequence of operations can be hard coded into the electronic circuit or soft coded by way of instructions held in a memory device. The function, operation, or sequence of operations can be performed using digital values or using analog signals. In some embodiments, the processor or controller can be embodied in an application specific integrated circuit (ASIC), which can be an analog ASIC or a digital ASIC, in a microprocessor with associated program memory, in a digital signal processor (DSP), and/or in a discrete electronic circuit, which can be analog or digital. A processor or controller can include internal processors or modules that perform portions of the function, operation, or sequence of operations. Similarly, a module can include internal processors or internal modules that perform portions of the function, operation, or sequence of operations of the module. A single processor or other unit may fulfill the functions of several means recited in the claims.

As used in the claims or elsewhere herein, the term "comprising" does not exclude other elements or steps, and the indefinite article "a" or "an" does not exclude a plurality.

As used herein, the term "predetermined," when referring to a value or signal, is used to refer to a value or signal that is set, or fixed, in the factory at the time of manufacture, or by external means, e.g., programming, thereafter. As used herein, the term "determined," when referring to a value or signal, is used to refer to a value or signal that is identified by a circuit during operation, after manufacture.

Various embodiments of the concepts systems and techniques are described herein with reference to the related drawings. Alternative embodiments can be devised without departing from the scope of the described concepts. It is noted that various connections and positional relationships (e.g., over, below, adjacent, etc.) are set forth between elements in the claims, detailed description, and drawings. These connections and/or positional relationships, unless specified otherwise, can be direct or indirect, and the claimed inventions are not intended to be limiting in this respect. Accordingly, a coupling/connection of entities can refer to either a direct or an indirect coupling/connection, and a positional relationship between entities can be a direct or indirect positional relationship. As an example of an indirect positional relationship, references in the present description to element or structure A coupled/connected to element or structure B include situations in which one or more intermediate elements or structures (e.g., element C) is provided between elements A and B regardless of whether the characteristics and functionalities of elements A and/or B are substantially changed by the intermediate element(s).

Furthermore, it should be appreciated that relative, directional or reference terms (e.g. such as "above," "below," "left," "right," "top," "bottom," "vertical," "horizontal," "front," "back," "rearward," "forward," etc.) and derivatives thereof are used only to promote clarity in the description of the figures. Such terms are not intended as, and should not be construed as, limiting. Such terms may simply be used to facilitate discussion of the drawings and may be used, where applicable, to promote clarity of description when dealing with relative relationships, particularly with respect to the illustrated embodiments. Such terms are not, however, intended to imply absolute relationships, positions, and/or orientations. For example, with respect to an object or structure, an "upper" or "top" surface can become a "lower" or "bottom" surface simply by turning the object over. Nevertheless, it is still the same surface and the object remains the same.

The terms "disposed over," "overlying," "atop," "on top," "positioned on" or "positioned atop" mean that a first element, such as a first structure, is present on a second element, such as a second structure, where intervening elements or structures (such as an interface structure) may or may not be present between the first element and the second element. The term "direct contact" means that a first element, such as a first structure, and a second element, such as a second structure, are connected without any intermediary elements or structures between the interface of the two elements. The term "connection" can include an indirect connection and a direct connection.

In the foregoing detailed description, various features are grouped together in one or more individual embodiments for the purpose of streamlining the disclosure. This method of disclosure is not to be interpreted as reflecting an intention that each claim requires more features than are expressly recited therein. Rather, inventive aspects may lie in less than all features of each disclosed embodiment.

References in the disclosure to "one embodiment," "an embodiment," "some embodiments," or variants of such phrases indicate that the embodiment(s) described can include a particular feature, structure, or characteristic, but every embodiment can include the particular feature, structure, or characteristic. Moreover, such phrases are not necessarily referring to the same embodiment(s). Further, when a particular feature, structure, or characteristic is described in connection knowledge of one skilled in the art to affect such feature, structure, or characteristic in connection with other embodiments whether or not explicitly described.

The disclosed subject matter is not limited in its application to the details of construction and to the arrangements of the components set forth in the detailed description or illustrated in the drawings. The disclosed subject matter is capable of other embodiments and of being practiced and carried out in various ways. As such, those skilled in the art will appreciate that the conception, upon which this disclosure is based, may readily be utilized as a basis for the designing of other structures, methods, and systems for carrying out the several purposes of the disclosed subject matter. Therefore, the claims should be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

Other variations to the disclosed embodiments can be understood and effected by those skilled in the art in practicing the claimed invention, from a study of the drawings, the disclosure, and the appended claims.

The mere fact that certain measures are recited in mutually different dependent claims does not indicate that a combination of these measures cannot be used to obtain an advantage.

Any reference signs in the claims should not be construed as limiting the scope.

All publications and references cited herein are expressly incorporated herein by reference in their entirety.

The invention claimed is:

1. A motor comprising:
a stator having a plurality of split teeth, each split tooth including a first coil winding and a second coil winding, one or more of the split teeth including:
a first tooth portion that includes the first coil winding and a first permanent magnet having a first polarity; and
a second tooth portion that includes the second coil winding and a second permanent magnet having a second polarity opposite the first polarity; and
a magnet-free rotor having one or more salient features,
wherein the motor is configured to drive current through the first coil winding and the second coil winding to levitate the magnet-free rotor using a magnet-biased reluctance actuator principle and to rotate the magnet-free rotor using a flux-reversal operating principle, and
wherein the motor is configured to generate torque and rotational force independently.

2. The motor of claim 1 wherein the motor is a bearingless split-tooth slice motor.

3. The motor of claim 1 wherein the motor is configured to drive a blood pump.

4. The motor of claim 1 wherein flux of a first one of the plurality of split teeth is configured to be controlled independently from flux of other ones of the plurality of split teeth.

5. The motor of claim 1 wherein the one or more of the split teeth and their corresponding first permanent magnet and second permanent magnet are arranged such that at least some adjacent permanent magnets have opposite polarity.

6. The motor of claim 1 wherein for the one or more of the split teeth, one or both of the first permanent magnet and the second permanent magnet is attached to an end of the corresponding tooth portion.

7. The motor of claim 1 wherein for the one or more of the split teeth, one or both of the first permanent magnet and the second permanent magnet has a dimension that is wider than a dimension of the corresponding tooth portion.

8. The motor of claim 1 wherein for the one or more of the split teeth, one or both of the first permanent magnet and the second permanent magnet has a dimension that is equal to a dimension of the corresponding tooth portion.

9. The motor of claim 1 wherein the one or more of the split teeth, one or both of the first permanent magnet and the second permanent magnet has a dimension that is longer than a dimension of the stator.

10. The motor of claim 1 wherein a pole of the rotor has a value of about 35°.

11. The motor of claim 1 comprising multiple coils on one or more of the split teeth.

12. The motor of claim 1 wherein one or more of the plurality of split teeth are configured as temple stator teeth.

13. The motor of claim 1 wherein, for one or more of the plurality of split teeth, the first and second permanent magnets are buried in the respective first and second tooth portions.

14. A bearingless split-tooth slice motor comprising:
a stator having a plurality of split teeth each having two coil windings and one or more of which having two permanent magnets of opposite polarity;
a magnet-free rotor having a plurality of salient features; and a controller configured to:
drive current through the coil windings of the plurality of split teeth to levitate and rotate the magnet-free rotor, and
to independently generate torque and rotational force on the magnet-free rotor.

15. The bearingless split-tooth slice motor of claim 14 wherein the controller is configured to control flux of a first one of the plurality of split teeth independently from flux of other ones of the plurality of split teeth.

16. The bearingless split-tooth slice motor of claim 14 wherein for one or more of the plurality of split teeth and their corresponding two permanent magnets are arranged such that at least some adjacent permanent magnets have opposite polarity.

17. The bearingless split-tooth slice motor of claim 14 wherein for one or more of the plurality of split teeth, one or both of the two permanent magnets is attached to an end of the corresponding tooth portion.

18. The bearingless split-tooth slice motor of claim 14 wherein for one or more of the plurality of split teeth, one or both of the two permanent magnets has a dimension that is wider than a dimension of the corresponding tooth portion.

19. The bearingless split-tooth slice motor of claim 14 wherein for the one or more of the plurality of split teeth, one or both of the two permanent magnets has a dimension that is equal to a dimension of the corresponding tooth portion.

20. A system comprising:
a pump; and
a motor configured to drive the pump and including:
a stator having a plurality of split teeth each having two coil windings and one or more of which having two permanent magnets of opposite polarity;
a magnet-free rotor having one or more salient features; and
a controller configured to drive current through the coil windings of the plurality of split teeth to:
levitate and rotate the magnet-free rotor using a flux-reversal operating principle, and
independently generate torque and rotational force on the magnet-free rotor.

* * * * *